(12) United States Patent
Guyton et al.

(10) Patent No.: US 10,849,652 B2
(45) Date of Patent: Dec. 1, 2020

(54) DEVICES, SYSTEMS, AND METHODS FOR IMPROVING ACCESS TO CARDIAC AND VASCULAR CHAMBERS

(71) Applicant: Emory University, Atlanta, GA (US)

(72) Inventors: Robert A. Guyton, Atlanta, GA (US); Saimuralidhar Padala, Atlanta, GA (US)

(73) Assignee: Emory University, Atlanta, GA (US)

( * ) Notice: Subject to any disclaimer, the term of this patent is extended or adjusted under 35 U.S.C. 154(b) by 506 days.

(21) Appl. No.: 15/139,848

(22) Filed: Apr. 27, 2016

(65) Prior Publication Data

US 2016/0235439 A1 Aug. 18, 2016

Related U.S. Application Data

(62) Division of application No. 13/825,871, filed as application No. PCT/US2011/054932 on Oct. 5, 2011, now abandoned.

(Continued)

(51) Int. Cl.
*A61B 18/14* (2006.01)
*A61B 17/34* (2006.01)
(Continued)

(52) U.S. Cl.
CPC ...... *A61B 17/3423* (2013.01); *A61B 17/0057* (2013.01); *A61B 17/3439* (2013.01); *A61B 18/1482* (2013.01); *A61B 18/1492* (2013.01); *A61B 34/70* (2016.02); *A61M 37/00* (2013.01); *A61N 7/02* (2013.01); *A61B 18/1815* (2013.01); *A61B 2017/0061* (2013.01);
(Continued)

(58) Field of Classification Search
CPC .......... A61B 2018/00363; A61B 2018/00375; A61B 2018/00369
See application file for complete search history.

(56) References Cited

U.S. PATENT DOCUMENTS 4,837,285 A 6/1989 Berg et al.
5,080,660 A 1/1992 Buelna
(Continued)

OTHER PUBLICATIONS

"BioGlue: BioGlue Instructions for Use" [online], 2014, retrieved from the Internet , <URL:http://http://www.cryolife.com/images/stories/assets/docs/BG_Surgical_Adhesive_Syringe_IFU_dom.pdf> on Jun. 5, 2015.
(Continued)

*Primary Examiner* — Michael F Peffley
*Assistant Examiner* — Bo Ouyang
(74) *Attorney, Agent, or Firm* — Emory Patent Group

(57) ABSTRACT

Devices, systems and methods are provided for enhancing mechanical strength of tissue, allowing direct and secure access to cardiac and vascular structures, either through tiny incisions or percutaneously. The method for accessing a cardiac chamber or a vascular conduit may include providing an access channel into tissue of the chamber or the conduit. The method may also include providing an energy-transducing element configured to provide heat within the access channel. The method may further include applying energy to the tissue or a tissue-stabilizing composition injected into, around, or adjacent to the tissue to mechanically enhance the access channel.

19 Claims, 21 Drawing Sheets

Related U.S. Application Data

(60) Provisional application No. 61/389,936, filed on Oct. 5, 2010.

(51) Int. Cl.

| | | |
|---|---|---|
| *A61B 17/00* | (2006.01) | |
| *A61B 34/00* | (2016.01) | |
| *A61M 37/00* | (2006.01) | |
| *A61N 7/02* | (2006.01) | |
| *A61B 18/00* | (2006.01) | |
| *A61B 18/18* | (2006.01) | |
| *A61N 1/05* | (2006.01) | |

(52) U.S. Cl.
CPC ............ *A61B 2017/00243* (2013.01); *A61B 2017/00606* (2013.01); *A61B 2017/00659* (2013.01); *A61B 2017/3425* (2013.01); *A61B 2018/0016* (2013.01); *A61B 2018/0063* (2013.01); *A61B 2018/00351* (2013.01); *A61B 2018/00577* (2013.01); *A61M 2037/0007* (2013.01); *A61M 2210/125* (2013.01); *A61N 1/0592* (2013.01); *A61N 7/022* (2013.01); *A61N 2007/025* (2013.01)

(56) References Cited

U.S. PATENT DOCUMENTS

| | | | |
|---|---|---|---|
| 5,292,362 A | 3/1994 | Bass et al. | |
| 5,387,247 A | 2/1995 | Vallana et al. | |
| 5,456,662 A | 10/1995 | Edwards et al. | |
| 5,546,954 A | 8/1996 | Yamada | |
| 5,607,463 A | 3/1997 | Schwartz et al. | |
| 5,649,951 A | 7/1997 | Davidson | |
| 5,690,670 A | 11/1997 | Davidson | |
| 5,725,573 A | 3/1998 | Dearnaley et al. | |
| 5,782,908 A | 7/1998 | Cahalan et al. | |
| 5,827,271 A * | 10/1998 | Buysse .............. | A61B 18/1206 606/40 |
| 5,875,782 A | 3/1999 | Ferrari et al. | |
| 5,891,507 A | 4/1999 | Jayaraman | |
| 5,897,911 A | 4/1999 | Loeffler | |
| 5,932,299 A | 8/1999 | Katoot | |
| 5,955,588 A | 9/1999 | Tsang et al. | |
| 5,980,563 A | 11/1999 | Tu et al. | |
| 6,010,500 A | 1/2000 | Sherman et al. | |
| 6,110,212 A | 8/2000 | Gregory | |
| 6,258,087 B1 | 7/2001 | Edwards et al. | |
| 6,267,781 B1 | 7/2001 | Tu | |
| 6,283,962 B1 | 9/2001 | Tu et al. | |
| 6,306,133 B1 | 10/2001 | Tu et al. | |
| 6,346,074 B1 | 2/2002 | Roth | |
| 6,355,030 B1 | 3/2002 | Aldrich et al. | |
| 6,463,332 B1 * | 10/2002 | Aldrich ................ | A61B 18/148 607/100 |
| 6,485,489 B2 | 11/2002 | Teirstein et al. | |
| 6,882,885 B2 | 4/2005 | Levy, Jr. et al. | |
| 7,048,733 B2 | 5/2006 | Hartley et al. | |
| 2005/0240200 A1 | 10/2005 | Bergheim | |
| 2006/0135953 A1 | 6/2006 | Kania et al. | |
| 2007/0112422 A1 | 5/2007 | Dehdashtian | |
| 2007/0270793 A1 | 11/2007 | Lattouf | |
| 2008/0208184 A1 | 8/2008 | Davies | |
| 2008/0215008 A1 | 9/2008 | Nance et al. | |
| 2009/0093670 A1 * | 4/2009 | Annest ............. | A61B 17/00234 600/16 |
| 2009/0287183 A1 * | 11/2009 | Bishop .............. | A61M 25/0662 604/509 |
| 2010/0069849 A1 | 3/2010 | Kassab | |
| 2010/0241118 A1 * | 9/2010 | Akahane ................ | A61B 1/018 606/41 |
| 2011/0270239 A1 * | 11/2011 | Werneth ............. | A61B 17/3478 606/33 |

OTHER PUBLICATIONS

Hsien et al. "Direct Transthoracic Access to the Left Ventricle for Catheter Ablation of Ventricular Tachycardia" Circulation: Arrhythmia and Electrophysiology, 2010, 3(2): 178-185.

Levy et al. "Percutaneous Direct Cardiac Catheterization: A New Method, with Results in 122 Patients" New England Journal of Medicine, 1964; 271(6): 273-280.

Lui et al. "The Use of Type I and Type III Injectable Human Collagen for Dermal Fill: 10 Years of Clinical Experience in China" Seminars in Plastic Surgery, 2005; 19(3): 241-250.

Nguyen et al. "Different Techniques of Distal Aortic Repair in Acute Type A Dissection: Impact on Late Aortic Morphology and Reoperation" European Journal of Cardio-Thoracic Surgery, 1999; 15(4): 496-501.

Nomori et al. "Gelatin-Resorcinol—Formaldehyde-Glutaraldehyde Glue-Spread Stapler Prevents Air Leakage from the Lung" The Annals of Thoracic Surgery, 1997; 63(2): 352-355.

Pasic et al. "Transapical Aortic Valve Implantation in 175 Consecutive Patients: Excellent Outcome in Very High-Risk Patients" Journal of the American College of Cardiology, 2010; 56(10): 813-820.

"ReCor Announces Successful First-In-Human Clinical Case Using Ultrasound to Cure Mitral Regurgitation (MR)." [online], Business Wire, 2010, retrieved from from the Internet <URL:http://http://www.businesswire.com/news/home/20100922006237/en/ReCor-announces-successful-first-in-human-clinical-case-ultrasound#.VZrHy_IVhBc> on Jun. 4, 2015.

"The Next Wave in Minimally Invasive Surgery" [online], Medical Device & Diagnostic Industry Magazine, 1998, retrieved from the Internet <URL:http://www.mddionline.com/article/next-wave-minimally-invasive-surgery> on Jun. 4, 2015.

Walther et al. "Human Minimally Invasive Off-Pump Valve-in-a-Valve Implantation" The Annals of Thoracic Surgery, 2008; 85(3): 1072-1073.

Office Action dated Mar. 11, 2015, by the Examiner in U.S. Appl. No. 13/825,871.

Office Action dated Oct. 27, 2015, by the Examiner in U.S. Appl. No. 13/825,871.

* cited by examiner

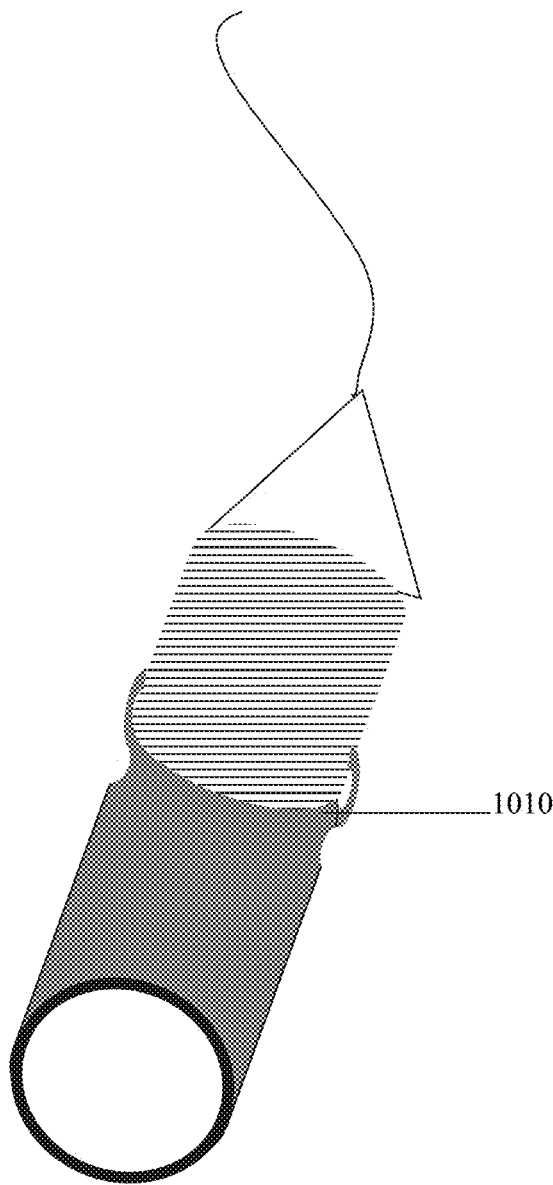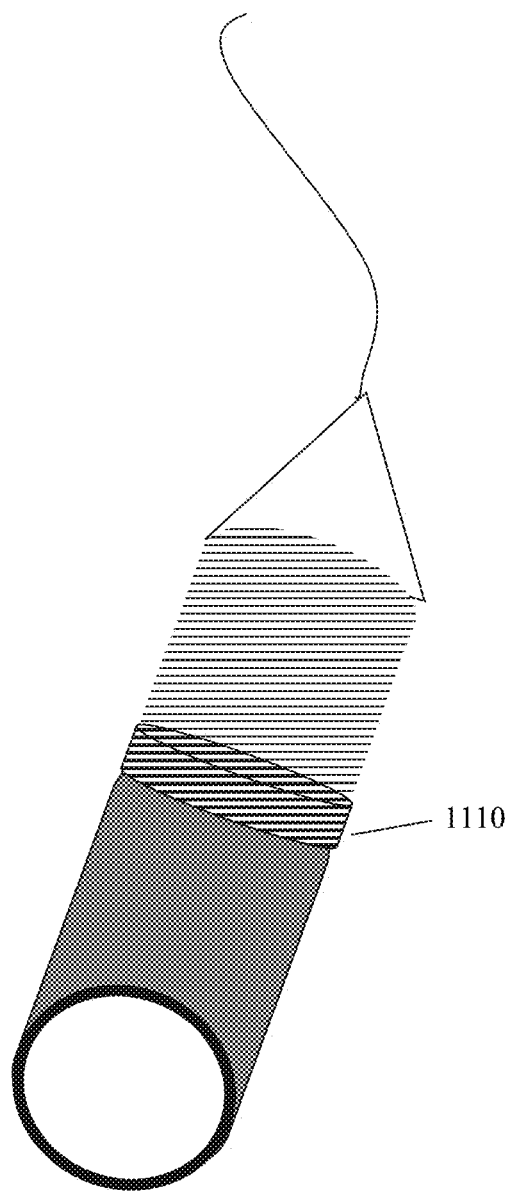
FIG. 10
FIG. 11

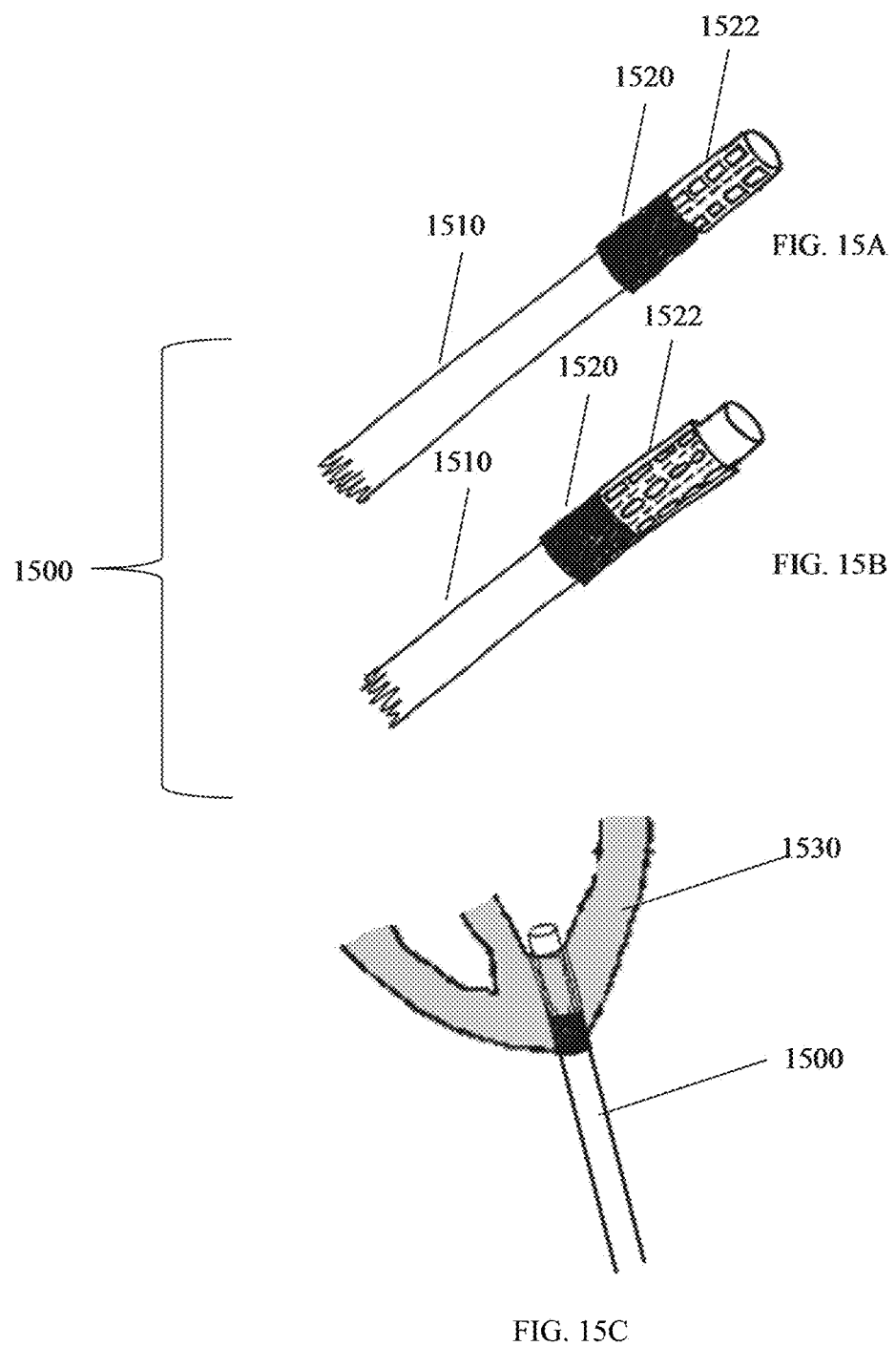

DEVICES, SYSTEMS, AND METHODS FOR IMPROVING ACCESS TO CARDIAC AND VASCULAR CHAMBERS

CROSS REFERENCE TO RELATED APPLICATIONS

This application is a division of U.S. application Ser. No. 13/825,871 filed Mar. 25, 2013, which is a National Stage of International Application Number PCT/US2011/054932 filed Oct. 5, 2011, which claims priority to U.S. Provisional Application No. 61/389,936 filed Oct. 5, 2010. The entirety of each of these applications is hereby incorporated by reference for all purposes.

FIELD

The present disclosure provides devices and methods for improved cardiac and vascular access to allow minimally invasive replacement or repair of cardiac and vascular structures. Such devices and methods rely on increasing the strength of the heart tissue or vascular wall to allow safer manipulation and reduced potential for catastrophic side effects.

BACKGROUND

Various types of surgical procedures are currently performed to investigate, diagnose, and treat certain cardiovascular disorders. Such procedures include repair and replacement of mitral, aortic, and other heart valves, repair of atrial and ventricular septal defects, pulmonary thrombectomy, treatment of aneurysms, electrophysiological mapping and ablation of the myocardium, and other procedures in which interventional devices are introduced into the interior of the heart or a vascular structure.

Using current techniques, many of these procedures require a gross thoracotomy to gain access into the patient's thoracic cavity and cardiac or vascular structures. A relatively large opening into the thoracic cavity is created through which the surgical team may directly visualize and operate upon the heart and other thoracic contents. Open-chest valve replacement surgery has the benefit of permitting the direct implantation of the replacement valve at its intended site. This method, however, is highly invasive and often results in significant trauma, risk of complications, as well as an extended hospitalization and a painful recovery period for the patient.

Minimally invasive valve replacement procedures have emerged as an alternative to open-chest surgery. Two types of minimally invasive valve procedures that have emerged are percutaneous valve procedures and trans-apical valve procedures. Percutaneous valve procedures pertain to making small incisions in the skin to allow direct access to peripheral vessels or body channels to insert catheters. Trans-apical valve procedures pertain to making a small incision in or near the apex of a heart to allow valve access. Because minimally invasive approaches require smaller incisions, they generally allow for faster patient recovery with less pain and bodily trauma. This, in turn, reduces the medical costs and the overall disruption to the life of the patient.

Minimally invasive trans-apical valve replacement procedures have emerged as an alternative to both open chest surgery and percutaneous valve surgeries. The use of minimally invasive approaches, however, highlights certain complexities in the surgery. Unlike open heart surgery, minimally invasive heart surgery offers a small surgical field that greatly reduces the surgeon's field of view and, consequently, the ability of the surgeon to detect complications as they arise. U.S. Patent Publication No. 2005/0240200 to Bergheim et al. presents certain methods and systems for the repair, removal, and/or replacement of heart valves through the apex of the heart. Similarly, U.S. Patent Publication No. 2007/0112422 to Dehdashtian provides a delivery system and method for delivering heart valves via a device that passes through the apex of the left ventricle.

Although there are a number of methods and devices available to assist in these procedures, the incidence of complications remains high, particularly in high risk and elderly populations. See for example, Hsieh, et al. 2010 *Circulation*: Arrhyth. Electrophys. 3:178-185, Pasic, et al. (2010) *J. Am. Coll. Cardiol.* 56:813-20 and Walther et al (2008) *Ann Thorac Surg.* 85(3): 1072-1073.

SUMMARY

There remains a need for improved methods and devices that allow the surgical manipulation through trans-apical or trans-cardiac wall access while reducing the likelihood that a patient's heart muscle will weaken or tear and release the access device. If such methods and devices can provide security from bleeding and tissue disruption during and after the period of access to the cardiac chambers or vascular structure, then such access may not require even a minimally invasive incision or thoracotomy, but may be performed percutaneously, potentially under local anesthesia.

In some embodiments, the disclosure relates to the use of certain devices, compositions and methods for enhancing the strength of tissue at a cardiac and/or vascular chamber access site (also referred to access channel). In some embodiments, the disclosure provides methods, systems and devices that are configured or structured to stabilize the access channel by mechanically enhancing or strengthening the access channel. In some embodiments, the methods, systems, and devices relate to delivering energy to stabilize the access channel. In other embodiments, the methods, systems, and devices relate to delivering a tissue-stabilizing composition to stabilize the access channel in addition to or in alternative of delivering energy to stabilize the access channel.

In some embodiments, the disclosure relates to heart access devices and systems. The heart access devices and systems may be configured or structured to provide a mechanically enhanced access channel within tissue or muscle of the heart. According to some embodiments, the heart access device may include a sheath including an open channel configured or structured to accept an interventional device, the sheath being configured to be inserted into the access channel. The heart access device may further include at least one energy-transducing component configured to deliver energy to tissue surrounding the sheath, the energy-transducing component being configured to cause the surrounding tissue to stabilize around the sheath. The heart access device may include a plurality of energy-transducing components, the plurality of energy-transducing components being disposed in a pattern. In some embodiments, the energy-transducing component may be configured to heat a tissue-stabilizing composition.

In some embodiments, the heart access device may include a sleeve. The sleeve may include the at least one energy-transducing component. The sleeve may be configured to surround the sheath. The sleeve may be configured to be movable with respect to the sheath.

In other embodiments, the device may include an introducer configured to form the access channel. In some embodiments, the sleeve may be configured to surround the introducer.

In some embodiments, the device may include a sheath including an open channel configured to accept an interventional device; and an introducer including at least one least one energy-transducing element configured to delivery energy. The open channel of the sheath may be configured to accept the introducer, the introducer being movably disposed with respect to the sheath. The open channel may also be configured to accept another device configured to manipulate a valve or inner cardiac chamber of the heart. The introducer may include an inner channel configured to accept a guidewire.

In some embodiments, the introducer may include a section that has a cross section that is equal or slightly less than a diameter of the inner channel of the sheath. The introducer may include a puncture tip. In some embodiments, the introducer may include a guide member having a cross section that is larger than an inner diameter of the inner channel.

In some embodiments, the device may further include a power source, the power source configured to deliver power to the at least one energy-transducing element. In some embodiments, the sheath may include at least one energy focusing or dispersing element, the at least one energy focusing element being configured to focus the energy on at least one of surrounding tissue or a tissue-stabilizing composition surrounding a portion of the heart access device. The at least one energy focusing component may correspond to or compliment the energy-transducing component. In some embodiments, the energy-transducing component may be configured to deliver microwave, ultrasound, radiofrequency (RF), or heat energy.

In some embodiments, the device may further include a sealing device configured to seal the access channel. The sealing device may be a plug. In some embodiments, the sealing device may be of a wound bioabsorbable material and/or a pre-formed hydrophilic material. In further embodiments, the sealing device may further include a base. The base may include an open channel configured to be disposed on a sealing device delivery device, such as an introducer. In some embodiments, the sealing device may further include extending members that extend from an elongated section constructed or made of a wound bioabsorbable material and/or a pre-formed hydrophilic material. The extending members may be constructed or made of a bioabsorable material. In some embodiments, the sealing device may further include a clip member. The clip member may be constructed or made of a memory shape alloy.

In some embodiments, the device may further include a sealing device introducer, the sealing device introducer configured to be anchor the sealing device within the access channel. The sealing device introducer may include external threads and the sheath may include internal threads, the threads of the sealing device introducer and the threads of the sheath being complementary. The sealing device introducer may further include a release mechanism configured to release the sealing device within the access channel.

In some embodiments, the sealing device may further include at least one sensor. The sensor may be configured to monitor cardiac conduction currents in myocardium. The sealing device may be configured to be anchored to the surrounding tissues by a fastener. The fastener may include one or more needles mounted in a pattern.

In some embodiments, the device may further include an energy source, the energy source configured to deliver energy through the heart access device. The heart access device may be configured to focus the energy on at least one of surrounding tissue or a tissue-stabilizing composition surrounding a portion of the heart access device.

In some embodiments, the disclosure provides a heart access device that may include a sheath including an open channel configured to accept an interventional device; and a delivery device configured to deliver a tissue-stabilizing composition into, around, or adjacent to the tissue surrounding the sheath, the tissue-stabilizing composition configured to mechanically enhance the tissue surrounding the sheath. In further embodiments, the heart access device may include an energy-transducing element configured to deliver energy to at least one of the tissue surrounding the sheath and the tissue-stabilizing composition, the energy-transducing component being configured to cause the surrounding tissue to stabilize around the sheath.

In some embodiments, the disclosure provides a device configured to provide access to the chambers of a beating heart or a vascular conduit. The device may include a sheath including an open channel configured to be inserted into a muscle of the heart or a wall of the vascular conduit to access an inner chamber of the heart or a vascular lumen of the vascular conduit, and configured to accept an interventional device. The device may include an introducer including atleast one energy-transducing element configured to deliver energy to the tissue surrounding the sheath for stabilization and strengthening. The device may also include sealing device configured to be delivered into the access channel.

The sealing device may be configured to close the access channel permanently or reversibly so that the access channel may be accessed at a later time.

In some embodiments, the sheath may include a section constructed of a material that conducts energy than remainder of the sheath. The sheath may include a section that has a different thickness than the remainder of the sheath. The sheath may include a section that is configured to focus energy to a specific location in the tissue surrounding the sheath.

The device may further include a sleeve. The sleeve may include at least one energy-dispersing element or energy-transducing element. The sleeve may be structured to surround the sheath. The sleeve may be movable with respect to the sheath. The device may further include an sealing device configured to be inserted into the open channel of the sheath, the introducer being disposed with respect to the sheath. The introducer may include a section having at least one or more energy-dispersing elements or energy-transducing elements. The energy-dispersing elements or energy-transducing elements being disposed in a pattern. The introducer may include an access channel.

The sleeve may include at least one energy-dispersing element or energy-transducing element configured to surround the introducer. The energy-transducing element may be configured to deliver a plurality of forms of energy, the forms may include heat, radio-frequency, ultra-sound or microwave. The sealing device may include a first section that is configured to close or seal the access channel and a second section configured to enable releasably attachment to a delivery introducer. The sealing device may be constructed of one of or any combination of a biological material, a biocompatible polymer, or a metal.

The device may further include a sealing device introducer configured to deliver the sealing device through the sheath into the access channel. The sealing device introducer may include threads on an outside surface and the sheath may include the threads within the channel. The threads of the sealing device introducer and the threads of the sheath may be complementary.

In certain embodiments, the disclosure provides a heart access device that allows insertion through a heart wall and includes an energy-transducing element on at least one portion of an insertion sleeve. In certain embodiments, the heart access device may include a sheath with an open channel configured to accept an interventional device. In further embodiments, the device may include a sleeve that is attached to or makes up at least a part of the sheath, wherein the sleeve is configured to provide energy to a surrounding tissue. In certain embodiments, the sleeve may be configured to heat the surrounding tissue. In other embodiments, the energy-transducing element (device) may be introduced separately from the sleeve during the procedure. In some embodiments, the heart access device may include a sheath with an open channel configured to accept an interventional device, and a sleeve that is attached to or makes up at least a part of the sheath, wherein the sleeve is configured to provide a tissue strengthening composition to surrounding tissue. Typically, the sleeve may be a sheath, tube or cannula. The sleeve is typically configured so as to provide a rigid channel through the wall of the heart. Typically, the sleeve may include an energy-transducing element on its tip. In certain embodiments, the element may be a heating element. In some embodiments, the element may surround the sleeve. The element may include coils that surround the sleeve. The element may be typically configured to surround the sleeve for at least 3 mm, or at least 6 mm, or at least 9 mm, or at least 12 mm, or at least 15 mm. Typically, the element may surround the sleeve for a distance sufficient to contact a portion of the tissue at the wall of a heart, but does not expand beyond the wall of the heart.

The energy-transducing element may be a mechanism for providing high frequency energy, which can include radiofrequency, ultrasound or microwave energy. In some embodiments, the sleeve may include a tissue contacting member that includes an array of electrodes which can penetrate the tissue surrounding the sleeve. Typically, the electrodes may include a radiofrequency electrode, a focused ultrasound electrode (i.e. transducer) or a combination of these. In some embodiments, the sleeve may include a tissue contacting coil for generating heat. The term "heating element" as used herein encompasses elements that apply energy thereby inducing heat in the tissue as well as to elements that apply heat to the tissue. In a preferred embodiment, the tissue may be heated to a temperature in the range of about 40 degrees Celsius to about 110 degrees Celsius, more preferably about 60 degrees Celsius to about 65 degrees Celsius.

In some embodiments, the disclosure provides a method of accessing a cardiac chamber including: (i) providing an access channel into the chamber; (ii) providing an energy-transducing element configured to provide heat or to cool tissue surrounding the access channel; and (iii) applying energy to the tissue. In certain embodiments, the method may further include modifying the tissue with a strength-enhancing compound (may also be referred to as a "tissue-stabilizing composition" or "tissue-stabilizing compound") prior to applying the energy. In some embodiments, the energy-transducing element may heat the tissue.

In some embodiments, the disclosure provides a method for accessing a cardiac chamber or a vascular conduit. The method may include: providing an access channel into tissue of the chamber or the conduit; providing an energy-transducing element configured to provide heat within the access channel; and applying energy to the tissue or a tissue-stabilizing composition injected into the tissue to mechanically enhance the access channel. The energy may be applied to the tissue, and the energy heats the tissue. In some embodiments, the method may further include delivering the tissue-stabilizing composition prior to applying the energy. The energy may additionally or alternatively be applied to the tissue-stabilizing composition.

In other embodiments, the disclosure provides a method of accessing a cardiac chamber including: (i) providing an access channel into the chamber; (ii) modifying the tissue surrounding the access channel with a strength-enhancing compound; and (iii) closing the access channel.

In some embodiments, the method may further include delivering a tissue-stabilizing composition prior to applying the energy. The energy may be applied to the tissue-stabilizing composition. In further embodiments, the method may further include positioning or inserting a sealing device into the access channel.

BRIEF DESCRIPTION OF THE FIGURES

The disclosure can be better understood with the reference to the following drawings and description. The components in the figures are not necessarily to scale, emphasis being placed upon illustrating the principles of the disclosure.

FIG. 2A shows a guidewire being inserted through a trocar into the tissue. FIG. 2B shows retraction of the needle. FIG. 2C shows the rotational insertion of a catheter over the guidewire to increase the diameter of the access port. FIG. 2D shows insertion of the sheath into the access port.

FIGS. 10 and 11 show a heart access device including a fastener according to embodiments.

FIGS. 15A-15C show a heart access device according to different embodiments.

DETAILED DESCRIPTION

The present disclosure provides methods, devices, and systems for providing access to the heart or heart vessels to perform cardiovascular surgery. The access may be provided by forming an access channel through the heart tissue or muscle (the myocardium).

The methods may include the step of, and devices, and systems may be configured or configured to provide stable access to the heart tissue or muscle. The methods, devices, and systems are configured or structured to stabilize the heart muscle or tissue surrounding the access channel so as to prevent the release of an access device. The methods, devices, and systems include a heart access device that includes a sheath. The methods, devices, and systems are configured or structured to stabilize the heart muscle or tissue surrounding the sheath so as to prevent the release of an access device. The methods, devices, and systems are configured or structured to mechanically enhance (strengthen) the tissue of the access channel.

In some embodiments, the methods may include the step, devices and systems may be configured or structured to deliver heat or energy passively to the heart tissue through the sheath causing the heart tissue to shrink tightly around the sheath and seal the tissue around the sheath. This results in stable access to the channel inside the sheath to perform interventional and diagnostic procedures. The energy may be applied by transducers provided on a wall of the sheath (directly or indirectly by a sleeve) or by a heating element or energy source (e.g., high-energy focused ultrasound) built into an introducer.

In other embodiments, the methods may include the steps of, and devices, and systems may be configured to deliver a tissue-stabilizing composition. in addition to or in alternative to delivering energy, to the surrounding tissue. The tissue-stabilizing composition may further mechanically enhance or stabilize the access channel.

According to embodiments, because the tissue surrounding the sheath has been stabilized (mechanically enhanced), it is possible to seal the access channel with a sealing device.

General Method to Access the Heart

Transapical cardiac surgery is not a new procedure. Levy and Lillehei described a technique for percutaneous direct cardiac catheterization in 1964 (Levy and Lillehei (1964) *NEJM* 271:273-280). The technique has been used since then, however percutaneous venous access is typically preferred. U.S. Patent Publication No. 2007/0112422 describes a general method and device for transapical heart valve delivery system. The method generally includes inserting an instrument through the subject's chest wall and through the heart wall. The instrument carries on its distal end a movable element which is manipulated to grasp a valve leaflet and hold it while a needle mechanism punctures the valve leaflet and loops a suture around a portion of the valve leaflet.

Figure 1:
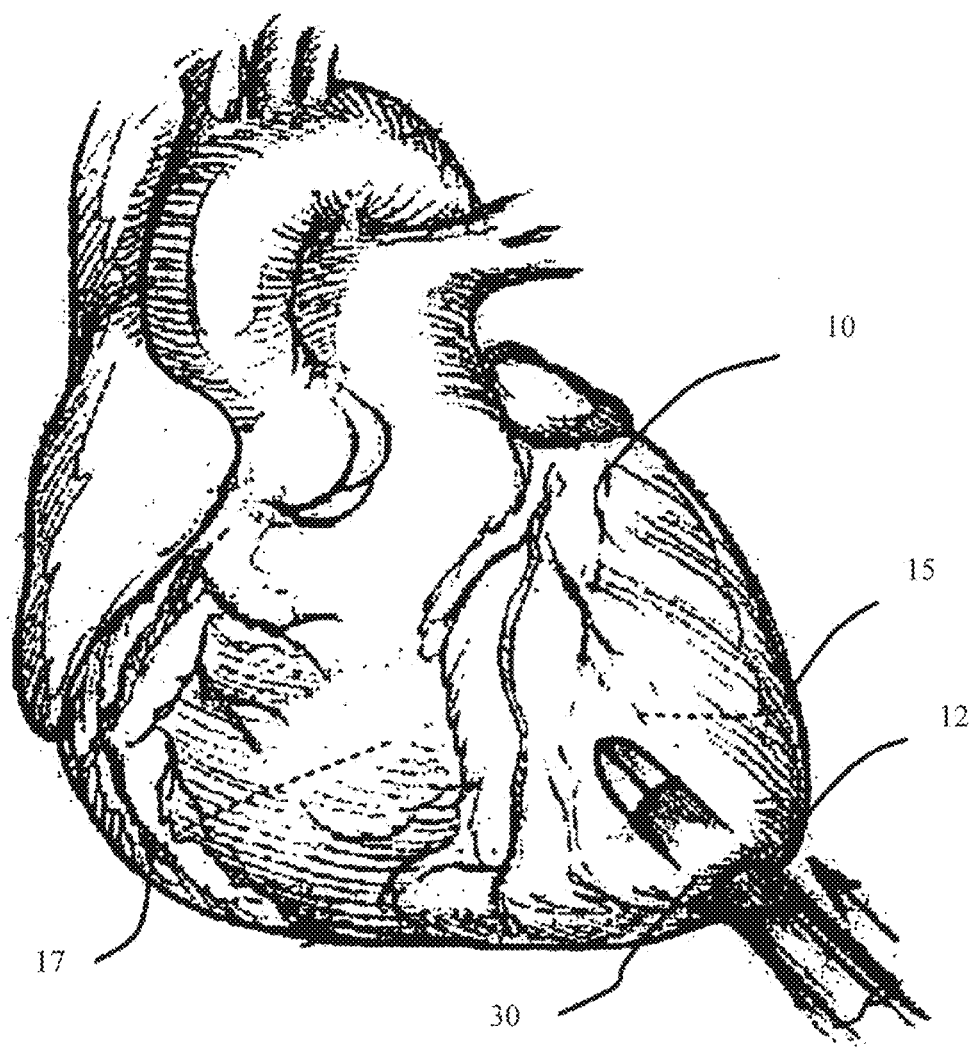
FIG. 1 is a diagram of the heart, showing an access port or channel through the apex.
Figure 2A:
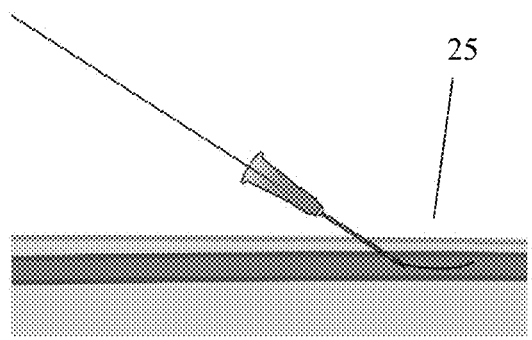
FIGS. 2A-2D are diagrams detailing the Seldinger method for providing tissue access according to embodiments.
Figure 2B:
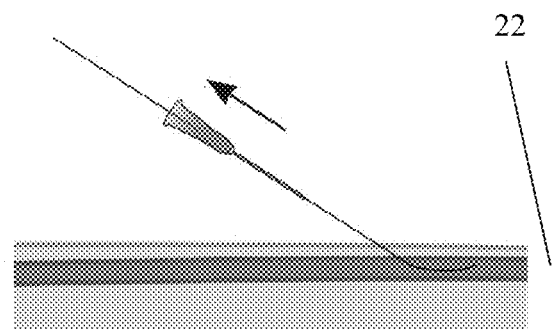
Figure 2C:
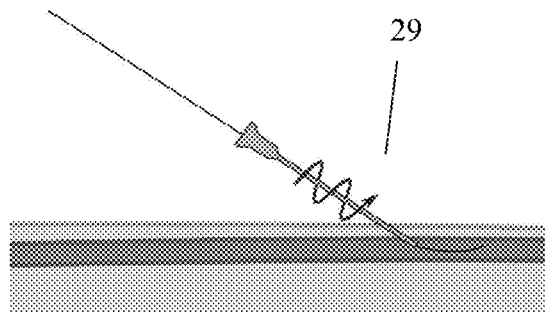
Figure 2D:
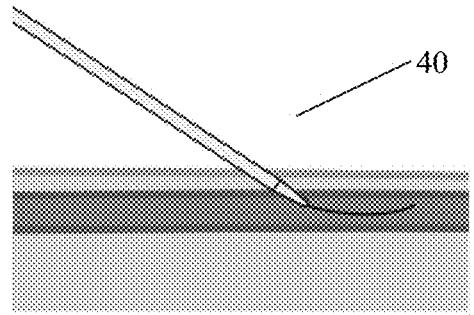

A general method of introducing a stent or sleeve into a heart apex is diagrammed in FIG. 1. The access system 30 is shown penetrating through the apex 12 of the heart 10. The moving direction of the access system is indicated by the arrow. The access system may enter either the right ventricle 17 or the left ventricle 15. To access the aortic or mitral valve, the access system typically passes through the left ventricle. This yields direct access to the aortic or mitral valve. To access the pulmonary or tricuspid valve, the access system would typically pass through the right ventricle.

The access system is diagrammed in FIG. 2. Typically, the technique used is the Seldinger technique for progressive dilation of the access channel. The access channel may be formed in a blood vessel as shown in FIG. 2 or in a cavity, such as a heart chamber as shown in FIG. 1. An access system 25 (here shown as a typically sharp hollow needle called a trocar) may be used to puncture the desired vessel or cavity, with ultrasound guidance if necessary to form an access channel. A round-tipped guidewire 22 may then advance through the lumen of the trocar, and the trocar is withdrawn. A blunt cannula or introducer 29 may then be passed over the guidewire into the cavity or vessel to increase the size of the opening. In the alternative, an introducer having a puncture tip at the end may be used to puncture the desired vessel or cavity. After the opening is of the appropriate size, a tube or sheath 40 may be introduced, in this instance including a sleeve as described herein and the guidewire may be withdrawn.

The tube or sheath 40 may be used to introduce catheters or other devices to perform endoluminal (inside the hollow organ) procedures, such as angioplasty. Fluoroscopy may be used to confirm the position of the catheter and to maneuver it to the desired location. Injection of radiocontrast may be used to visualize organs. Interventional procedures, such as thermoablation, angioplasty, embolization or biopsy, may be performed. Upon completion of the desired procedure, the access port may be closed as described herein and the tube or sheath may be withdrawn. In certain embodiments, a sealing device may be used to close the hole made by the procedure.

In addition to grasping and needle mechanisms, instruments used for repair procedures often include fiber optics that provide direct visual indication that the valve leaflet is properly grasped. A set of illuminating fibers terminate at the distal end of the instrument around the needle mechanism in close proximity to a set of sensor fibers. The sensor fibers may convey light from the distal end of the instrument to produce an image for the operator. When a valve leaflet is properly grasped, light from the illuminating fibers may be reflected off the leaflet surface back through the sensor fibers. On the other hand, if the valve leaflet is not properly grasped, the sensor fibers may sense or view blood.

The present disclosure provides methods, devices and systems for performing cardiovascular surgery, wherein access to the heart or great vessels may be provided through the heart muscle. In preferred embodiments, access may be provided through the apical area of the heart. The apical area of the heart is generally the blunt rounded inferior extremity of the heart formed by the left and right ventricles. In normal healthy humans, it generally lies behind the fourth or fifth left intercostal space in the mid-clavicular line.

The unique anatomical structure of the apical area permits the introduction of various surgical devices and tools into the heart without significant disruption of the natural mechanical and electrical heart function. While access to the heart through peripheral (e.g. femoral, jugular, etc.) vessels in percutaneous methods are limited to the diameter of the vessel (approximately 1 to 8 mm), access to the heart through the apical area may be significantly larger (approximately 1 to 25 mm or more). Moreover, apical access is dramatically closer to intracardiac structures than access through peripheral vessels. Thus, apical access to the heart permits greater flexibility with respect to the types of devices and surgical methods that may be performed in the heart and great vessels.

It should be noted that while reference is made herein of trans-apical procedures, it is intended for such procedures to encompass access to the heart through any wall thereof, and not to be limited to access through the apex only. While the apical area is particularly well suited for the purposes of the present disclosure, for certain applications, it may be desirable to access the heart at different locations, all of which are within the scope of the present disclosure.

Devices and Systems

According to embodiments, the access devices and systems may be configured or structured to strengthen a patient's heart muscle so as to reduce the likelihood that the patient's heart muscle will weaken and release an access device.

In some embodiments, the access device may include at least one sheath. In some embodiments, the access device may include one sheath. In other embodiments, the access device may include one sheath that has more than one section. In certain embodiments, the access device may include more than one sheath. Each sheath may have one or more than one section.

Figure 3:
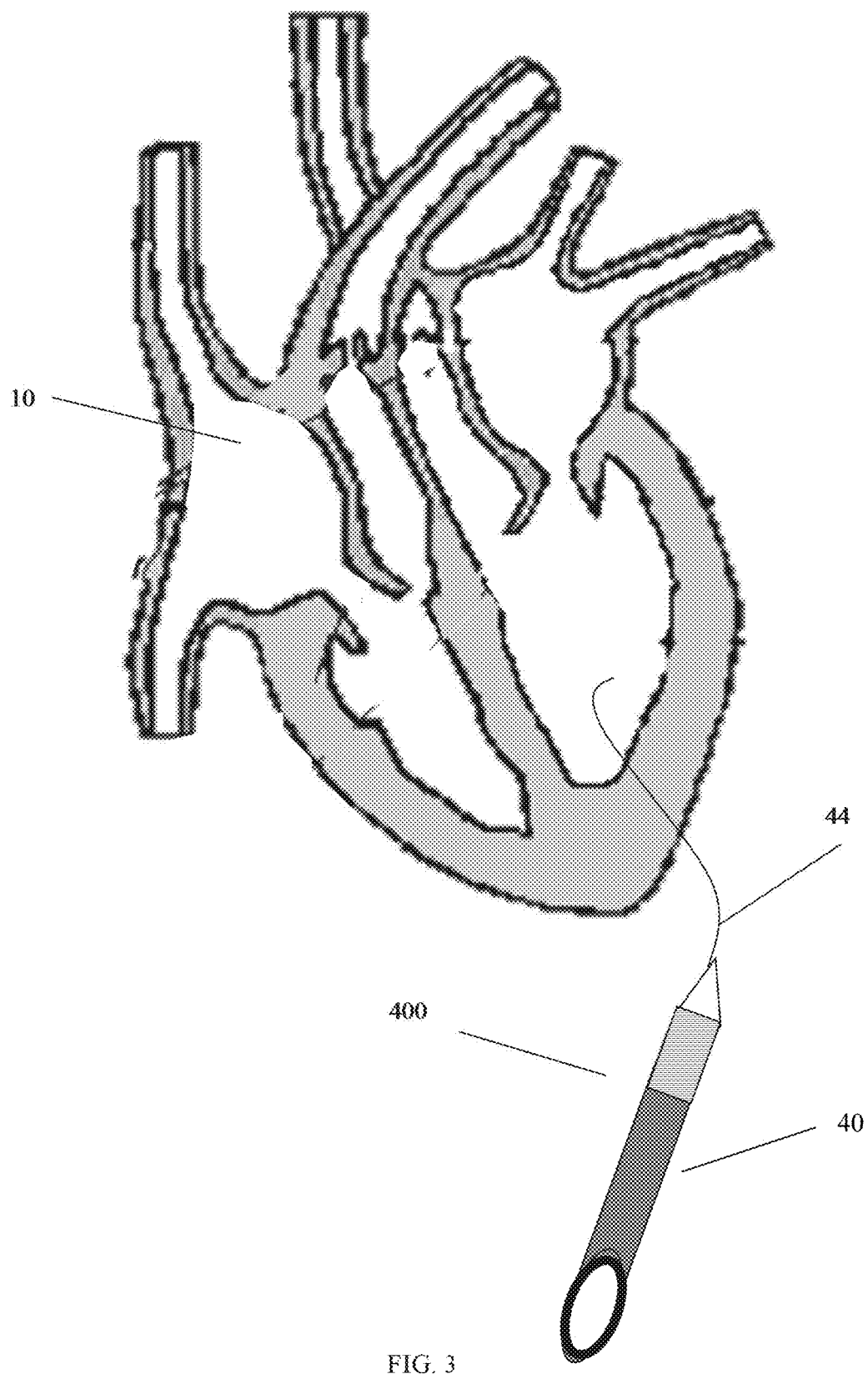
FIG. 3 shows the initial insertion of the sheath of the disclosure.
Figure 4:
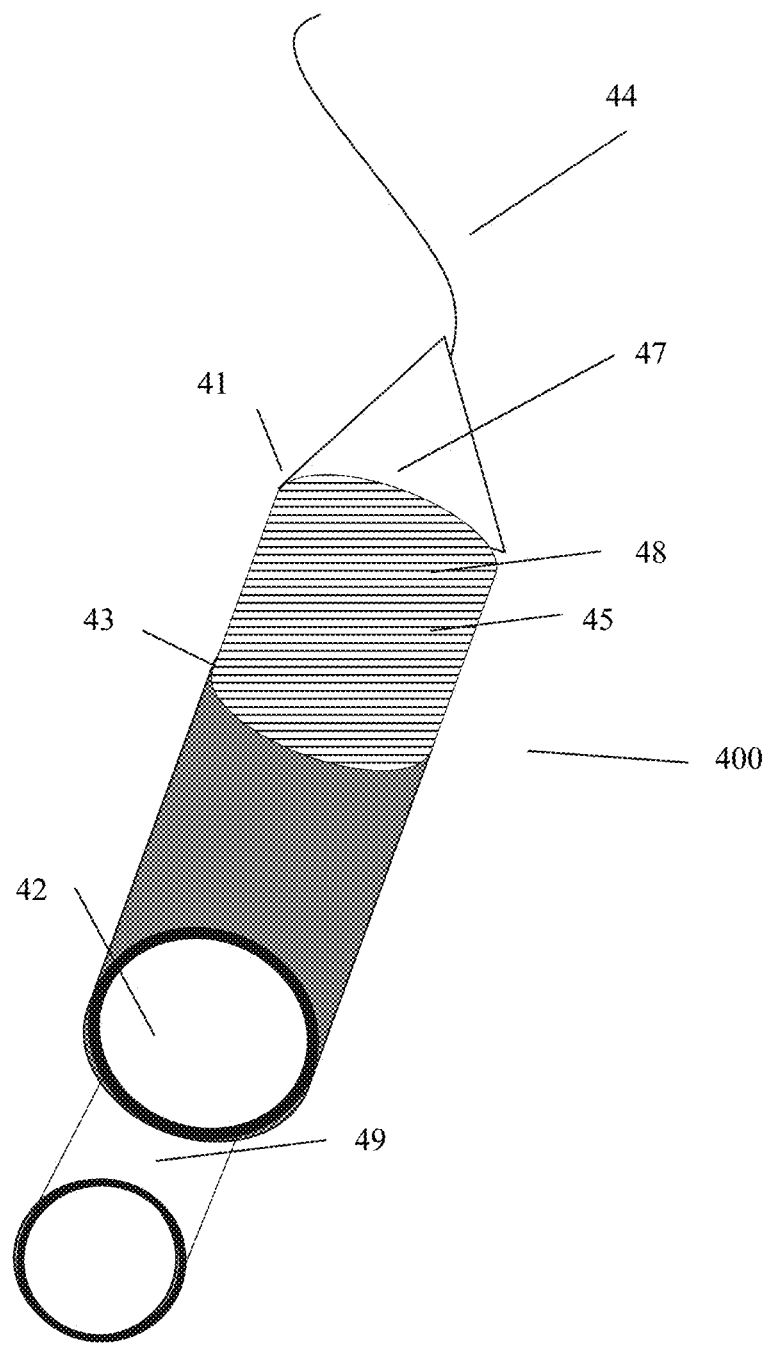
FIG. 4 is a diagram of a heart access device according to embodiments.

Referring to FIGS. 3 and 4, in some embodiments, the access device 400 may include the sheath 40. The sheath 40 may be of any shape. The sheath 40 may be in the form of an elongated tube. The sheath 40 may include an interior bore or channel 42 extending between its proximal and distal ends.

In certain embodiments, the sheath 40 may include more than one section. In some embodiments, the sheath 40 may include a first section that is relatively stiff and a second section that is relatively flexible. In certain embodiments, the sheath 40 may include a relatively stiff wall section extending from its distal end 41 to juncture 43 (also referred to as "distal section"), and a relatively limber wall section throughout the rest of the sheath (also referred to as "proximal section"). Alternatively, the sheath may have stiffness throughout its entirety.

The sheath 40 may be arranged so that at least one section is "torquable." That is, at least the proximal section of the sheath may be arranged to transmit torsional motion about its axis. Thus, by turning the proximal end of the sheath, the distal end of the sheath may also be rotated about an axis.

In some embodiments, the access device 400 may be configured to receive or accept and introduce medical instruments for procedures to be performed such interventional and diagnostic procedures to a chamber of the heart. The inner channel 42 of the sheath 40 may be configured to receive or accept medical instruments. In other embodiments, an end of the access device 400 may be configured to connect to an interventional and/or diagnostic device. The access device 400 may be configured to connect to a connecting device.

In some embodiments, the access device may be configured to introduce catheters or other devices to perform endoluminal (inside the hollow organ) procedures, such as angioplasty. Fluoroscopy may be used to confirm the position of the catheter and to maneuver it to the desired location. Injection of radiocontrast may be used to visualize organs. Interventional procedures, such as thermoablation, angioplasty, embolization, biopsy, or deployment of stents or replacement or repair valve devices may be performed.

The device 400 may be configured to receive or accept imaging devices. The system may also further include imaging devices. In addition to grasping and needle mechanisms, instruments used for repair procedures often include fiber optics that provide direct visual indication that the valve leaflet is properly grasped. A set of illuminating fibers terminate at the distal end of the instrument around the needle mechanism in close proximity to a set of sensor fibers. The sensor fibers convey light from the distal end of the instrument to produce an image for the operator. When a valve leaflet is properly grasped, light from the illuminating fibers is reflected off the leaflet surface back through the sensor fibers. On the other hand, if the valve leaflet is not properly grasped, the sensor fibers see blood.

The heart access device 400 may further include a manipulating instrument 44 that is slidably mounted thereon and that may be configured to be manipulated. The manipulating instrument 44 may be slidably mounted onto the sheath. The manipulating instrument 44 may be a guidewire.

Figure 8:
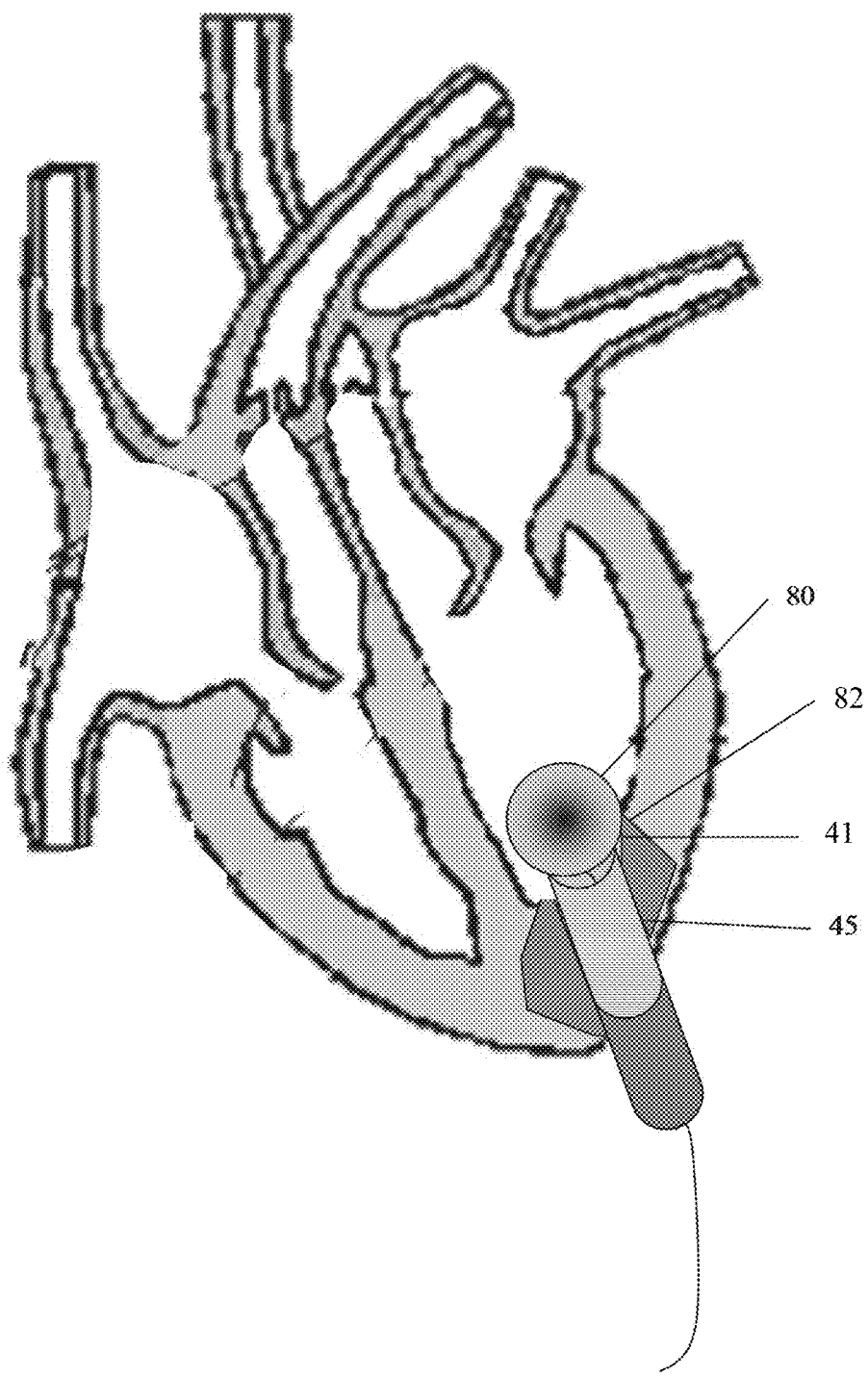
FIG. 8 shows inflation of a balloon to retract the sleeve into the appropriate position.

An expandable balloon may be advanced over the guide wire into the cardiac chamber, illustratively in the form of balloon 80. When inflated, as depicted in FIG. 8, the balloon may generally be in the form of a surface of revolution about a central axis coincident with proximal-to-distal axis of the catheter. The diameter of the balloon may typically be about 20 mm and may usually be formed from a polymer such as nylon with a wall thickness of about 8 microns to about 30 microns. When deflated, the balloon may collapse inwardly to form a relatively small diameter structure. The balloon may be fabricated by blow-molding using techniques that are known in the art. Typically, the balloon may be advanced after insertion of the sheath and expanded within the ventricle. After inflation, the balloon may then be pulled on to move the sleeve 45 so that the distal end of the sleeve is coincident with the interior of the tissue. This positioning of the sheath may be accomplished either before or after the tissue strengthening procedure.

In some embodiments, the access device may include at least one energy-transducing component or element. The energy-transducing component (also referred to as "energy-transducing element) may be configured to heat and thus denature collagen fibers and other proteins within the surrounding tissue. The energy-transducing element may be a mechanism for providing high frequency energy, which may include radiofrequency, ultrasound or microwave energy. The energy-transducing element may be a heating element configured to heat and thus denature collagen fibers within the surrounding tissue. In some embodiments, the energy-transducing element may be configured to deliver energy to the surrounding tissue as described herein. In further embodiments, the energy-transducing element may be configured to convert radio-frequency into heat. The energy-transducing component may be configured to transmit energy when connected to a power source.

In some embodiments, the access device 400 may include a sleeve 45. The sleeve 45 may include may have an interior bore or channel 47 extending between its proximal and distal ends.

In some embodiments, the sheath 40 may include the sleeve 45 that has an energy-transducing component 48, as shown in FIG. 4. In some embodiments, the sleeve 45 may be provided on all or a portion of the sheath 40. In other embodiments, the sleeve 45 may be attached to or extended from the sheath 40.

FIGS. 15(A)-(C) show another example of an access device including a sheath. In some embodiments, the energy-transducing component(s) may be disposed on a sleeve configured to be movably disposed around a sheath, as shown in for example, FIG. 15.

FIGS. 15(A)-(C) show an access device 1500 having a sheath 1510 with a sleeve 1520. The sleeve 1520 may include a plurality of energy-transducing components 1522. As shown in FIGS. 15(A) and 15(B) show how the sleeve 1520 may be configured to be movable with respect to the sheath 1510. FIG. 15(C) shows an example of the access device 1500 being positioned within an access channel in the myocardium 1530.

In other embodiments, the energy-transducing component(s) may be integrated with the sheath.

In some embodiments, the sleeve 45 may include one energy-transducing component. In other embodiments, the sleeve may include more than energy-transducing components. The sleeve may be typically made out of a thrombo-resistant, biocompatible material such as pyrolytic carbon. Pyrolytic carbon is a turbostratic carbon, which are materials that are structurally similar to graphite but have greater durability. The sleeve may also be made out of some material that can withstand heat.

In some embodiments, the energy-transducing component may include an ultrasonic transducer. In some embodiments, the heart access device may include a tubular, cylindrical ultrasonic transducer. The sleeve typically may include a tubular, cylindrical ultrasonic transducer. The transducer may be mounted on the sleeve. Such a transducer may be coaxial or nearly coaxial with the sleeve, and arranged so that the transducer extends axially over at least part of the sleeve. Merely by way of example, the transducer may have an axial length of about 6 mm and an outside diameter of about 2-3 mm. Typically, the proximal end of the transducer will not extend out of the tissue when the sleeve is anchored or placed within the heart. In some embodiments, the transducer may be formed from a ceramic piezoelectric material. The tubular transducer may have metallic coatings on its interior and exterior surfaces.

In some embodiments, the sheath 40 may include RF electrode wires inside the sleeve 45, and the electrodes are surrounded by an insulating sleeve axially moveable thereon; the sleeve is retracted to expose a predetermined portion of the electrode; and RF energy is applied to the tissue through the electrode to cause heating of the tissue. In other embodiments, an RF electrode wire is positioned on the sleeve 45 and is exposed to tissue upon insertion of the sleeve.

In some embodiments, the heart access devices and systems may further include a wiring support tube 49. The wiring support tube 49 may be provided within along all or a portion of the inner channel of the sheath. In further embodiments, the wiring support tube 49 may be provided within along all or a portion of the inner channel of the sleeve. In some embodiments, the wiring support tube may be connected to one of the sheath and/or the sleeve. The wiring support tube 49 may be provided at an end of the heart access device.

The heart access devices and systems may further include a catheter that is configured to deliver the wires to the transducer. The wires may be configured to extend through wiring support tube 49 to the distal end of the catheter. These wires may extend through the catheter to the proximal end of the catheter, and may be configured to be connected to an ultrasonic excitation or power source. Metallic support tubes and transducers may be typically configured so that the interior surface of the tubular transducer is spaced apart from the exterior surface of the tube by a gap distance which corresponds to approximately one-half the wavelength of the ultrasonic energy to be applied, i.e., about 83 microns for 9 MHz ultrasonic energy propagating in water. This promotes efficient operation of the transducer, with ultrasonic energy reflected at the exterior surface of support tube reinforcing ultrasonic energy propagating within the transducer, so as to provide ultrasonic energy directed outwardly from external surface of the transducer.

With the sleeve in place and in contact with the tissue, the energy-transducing element or component 48 may be configured to be activated. The energy-transducing element 48 may be activated by an energy or power source. In some embodiments, the energy-transducing element 48 may be configured to provide energy to surrounding tissue when the energy source is provided within an inner channel of sheath. In further embodiments, the energy source may be additionally or alternative provided within an inner channel of the sleeve 45.

In some embodiments, the energy source may be configured for ultrasound energy. In one embodiment, an ultrasonic excitation source may actuate the transducer to emit ultrasonic waves. In another embodiment, electrodes may be inserted into the tissue from the sleeve and either radiofrequency or microwaves are transferred through the system. Merely by way of example, ultrasonic waves may have a frequency of about 1 MHz to a few tens of MHz, most typically about 9 MHz. The transducer typically may be driven to emit, for example, about 10 watts to about 100 watts of acoustic power, most typically about 30 to about 40 watts. The actuation may be continued for about 20 seconds to about a minute or more, most typically about 40 seconds to about 90 seconds. Optionally, the actuation may be repeated several times as, for example, about 5 times. The frequencies, power levels, and actuation times may be varied from those given above. The ultrasonic waves generated by the transducer propagate generally radially outwardly from the transducer, outwardly through surrounding tissue. The ultrasonic waves impinge on the tissues of the heart surrounding the sleeve. The energy applied by the transducer is effective to heat and thus denature collagen fibers within the surrounding tissue. It is expected that, because the energy is dissipated and converted to heat principally inside the surrounding tissue, the procedure does not damage the surface of the heart that is in contact with the blood, and hence does not provoke thrombus formation.

When necessary, it is envisioned that the sheath may include a cooled liquid circulation system, such as a balloon, that will reduce the heat provided to the tissue through the sleeve. Circulation of the cooled liquid during the procedure helps to cool the transducer and essentially prevents direct heat transfer between the transducer and the epithelial lying at the surface of the tissue. However, it is typically expected that the regions of the epithelium that are not in contact with the sleeve are cooled by blood flowing over them during the procedure with continued operation of the heart.

In some embodiments, the heart access devices and systems may further include a wiring support tube 49. The wiring support tube 49 may be provided within along all or a portion of the inner channel of the sheath. In further embodiments, the wiring support tube 49 may be provided within along all or a portion of the inner channel of the sleeve. In some embodiments, the wiring support tube may be connected to one of the sheath and/or the sleeve. The wiring support tube 49 may be provided at an end of the heart access device.

In some embodiments, the heart access devices and systems may further include a catheter that is configured to deliver the wires to the transducer. The wires may be configured to extend through wiring support tube 49 to the distal end of the catheter. These wires may extend through the catheter to the proximal end of the catheter, and are configured to be connected to an ultrasonic excitation source. Metallic support tubes and transducers may be typically configured so that the interior surface of the tubular transducer is spaced apart from the exterior surface of the tube by a gap distance which corresponds to approximately one-half the wavelength of the ultrasonic energy to be applied, i.e., about 83 microns for 9 MHz ultrasonic energy propagating in water. This promotes efficient operation of the transducer, with ultrasonic energy reflected at the exterior surface of support tube reinforcing ultrasonic energy propagating within the transducer, so as to provide ultrasonic energy directed outwardly from external surface of the transducer. In some embodiments, the heart access devices and systems may further include an introducer. The introducer may be configured to puncture the tissue to create a channel. The introducer may be configured to be inserted into a sheath according to embodiments described herein.

Figure 12:
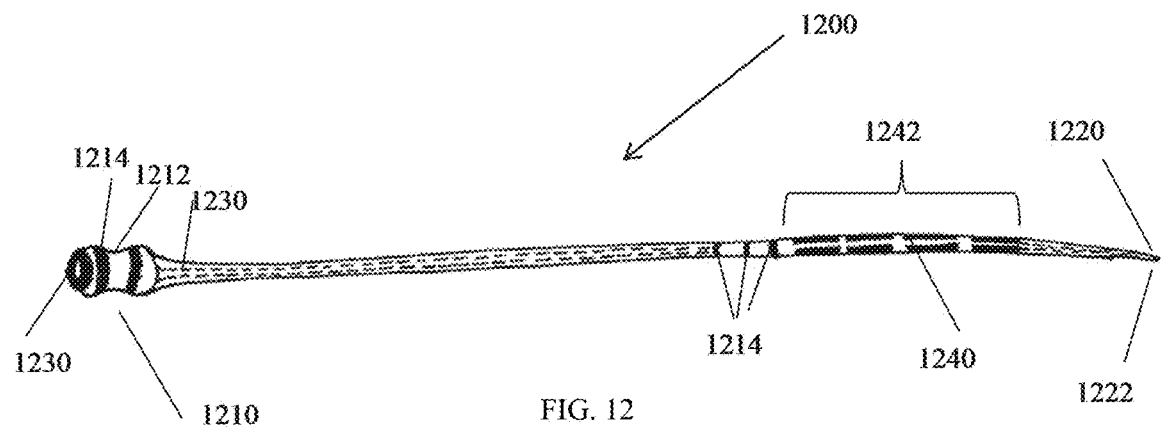
FIG. 12 shows an introducer according to embodiments.
Figure 13:
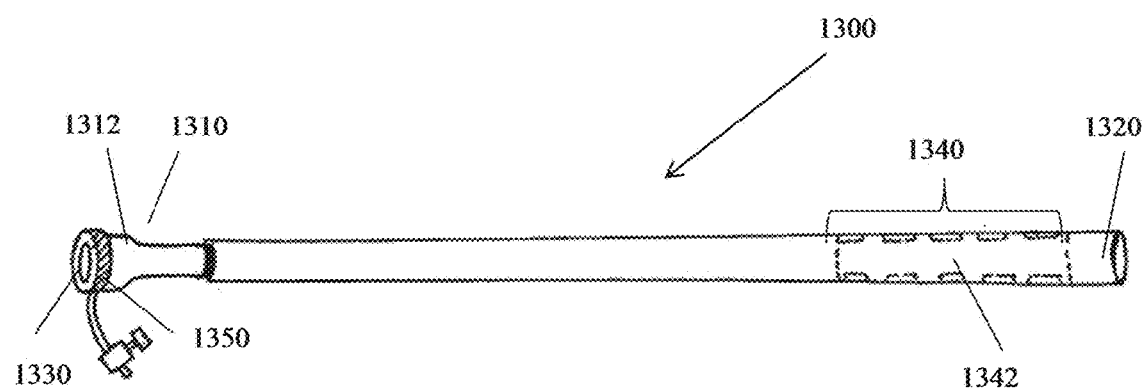
FIG. 13 shows a sheath according to embodiments.
Figure 14:
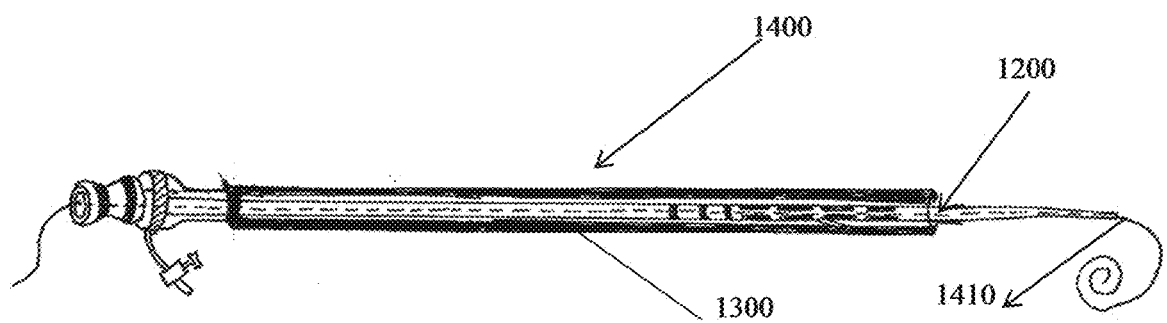
FIG. 14 shows a heart access device according to embodiments.

According to some embodiments, a heart access device may include a sheath and an introducer that includes an energy-transducing component. FIGS. 12-14 show an example of a heart access device according to these embodiments.

The introducer 1200 may include a first end 1210 and an opposing, second end 1220 (also referred to as proximal and distal ends, respectively), as shown in FIG. 12. In some embodiments, the introducer 1200 may have the same or different diameters along the length (between the first end 1210 and the second end 1220). The diameter of the introducer may be decrease or taper from the first end 1210 to the second end 1220. In some embodiments, the introducer may include one section that has the substantially the same diameter and another section that has a diameter that tapers.

In some embodiments, the introducer 1200 may include a guide member 1212 extending from or disposed at the proximal or first end 1210. The guide member 1212 may include an entrance to the interior bore or channel 1230. The guide member 1212 may have a larger diameter than the diameter of inner channel or bore of the sheath configured to receive the introducer 1200. The guide member 1212 may prevent the introducer from moving further within a sheath. The guide member 1212 may also be configured to form a tight seal with the sheath so as to prevent blood leakage.

In some embodiments, the introducer 1200 may include an inner bore or channel 1230 configured to receive or accept instruments. The channel 1230 may be configured to receive a guidewire, such as guidewire 44 or guidewire 1410. The guidewire may be a piggytail guidewire like guidewire 1410 shown in FIG. 14. The channel 1230 may also be configured to receive or accept an energy source.

In some embodiments, the channel 1230 may be along the entire length of the introducer. In other embodiments, the channel 1230 may be along a portion of the entire length of the introducer. In some embodiments, the channel 1230 may begin or have an entrance at the first end 1210. The guide member 1212 may also include an inner channel or bore that corresponds to channel 1230. The diameter of the channel 1230 may correspond to the diameter(s) of the introducer 1200. For example, the diameter of the channel 1230 may taper from a point between the first end 1210 and the second end 1220 towards the second end 1220.

The introducer 1200 may include a puncture tip 1222. The puncture tip 1222 may be configured to puncture tissue, such as the myocardium, to create an access channel within the tissue. The puncture tip 1222 may be solid. In other embodiments, the puncture tip 1222 may be hollow.

In some embodiments, the introducer 1200 may further include at least one energy-transducing component or element 1240. The energy-transducing component 1240 may correspond to any of the components described herein. The introducer 1200 may include one or more than one energy-transducing component 1240. In some embodiments, the introducer 1200 may include at least two, three or four transducing components.

In some embodiments, the energy-transducing component(s) may be integrated with the introducer 1200. In other embodiments, the energy-transducing component may be positioned on a sleeve. The sleeve may be configured to be fixedly disposed around an introducer as shown in FIG. 12.

The energy-transducing components may be provided in at least one region or section of the introducer or sheath that is configured to contact the tissue such as the myocardium. The energy-transducing region 1240 may be located near the distal end 1220 of the introducer, as shown in FIG. 12.

In some embodiments, the introducer 1200 may further include at least one marking configured to assist with the placement of the introducer. In some embodiments, the guide member 1212 may include a marking 1214. In other embodiments, the introducer may additionally or alternatively include markings 1214 along all or part of the length. In some embodiments, the markings 1214 may be positioned along the length so that they may be counted to ensure proper adjustment of the introducer 1200 relative to a sheath and/or the target site.

In some embodiments, the heart access device may further include a sheath 1300, as shown in FIG. 13. The sheath 1300 may be configured to accept or receive an introducer. The sheath 1300 may be similar to sheath 40. The sheath 1300 may be an elongated tube.

In some embodiments, the sheath 1300 may include an inner bore or channel 1330 along the length configured to receive or accept instruments. The channel 1330 may be configured to receive an introducer. The introducer may be the same or different from the introducers described herein.

The sheath 1300 may include a first end 1310 and an opposing, second end 1320 (also referred to as proximal and distal ends, respectively), as shown in FIG. 13. In some embodiments, the sheath 1300 may have the same or different diameters along the length (between the first end 1310 and the second end 1320).

In some embodiments, the sheath 1300 may include a guide member 1312 extending from or disposed at the proximal or first end 1310. The guide member 1312 may include an entrance to the interior bore or channel 1330. The guide member 1312 may have a portion that has larger diameter than the diameter of the length of the sheath. The guide member 1312 may prevent an introducer from moving further within the sheath.

In some embodiments, the sheath 1300 may include an inner bore or channel 1330 configured to receive or accept instruments. The channel 1330 may be configured to an introducer. The channel 1330 may be along the entire length of the sheath. The introducer 1200 may include a section that has a cross section that is equal or slightly less than a diameter of the channel 1330 of the sheath so that the channel may the introducer 1200 (but for the guide member).

In some embodiments, the length of the sheath 1300 may have a length that is shorter than or substantially equal to the length of the introducer 1200. As shown in FIG. 14, the introducer 1200 is longer than the sheath 1300.

The sheath 1300 may include at least one valve to prevent the leakage of the blood. In some embodiments, the sheath 1300 may include a valve 1350 on the guide member 1312. The valve 1340 may be a suction valve.

In some embodiments, the sheath 1300 may include more than one section. In some embodiments, the sheath 1300 may include an energy-dispersing or focusing section 1340. The energy-focusing section 1340 may be configured to contact or touch an outside surface of the introducer that includes the energy-transducing components.

The energy focusing section 1340 may include one or more than energy-dispersing or focusing elements 1342 (also referred to as components). The energy-dispersing or focusing elements 1342 may be configured to focus the energy from the energy-transducing components to a specific area of the tissue. The position and or pattern of the energy-dispersing or focusing elements 1342 may be based on the desired point(s) or location(s) of the tissue at which energy should be applied. The pattern of the energy-focusing elements may correspond to the pattern of the energy-transducing components provided on an introducer (in an associated manner). As shown in FIG. 13, the pattern of the energy-focusing elements 1342 may correspond to the pattern of energy-transducing components 1240.

The energy-focusing elements 1342 may depend on the energy-transducing components to be used. For example, if the energy-transducing components are ultrasound, the sheath does not need energy focusing elements 1342 to transmit or disperse the energy to the tissue. On the other hand, if the energy-transducing components are heat, the sheath may include energy focusing elements 1342 to transmit or disperse the energy to the tissue.

In some embodiments, the thickness of the sheath may vary. In some embodiments, the energy focusing section 1340 may be thinner than the other sections of the sheath.

FIG. 14 shows an example of an assembly of a heart access device 1400 having the introducer 1200 and the sheath 1300. As shown in FIG. 14, the diameter of the proximal or first ends of the introducer 1200 and the sheath 1300 may correspond to each other to prevent leakage of blood. In some embodiments, the diameter of the guide members 1212 and 1312 that may correspond to each other to prevent leakage of blood. The guide member 1212 of the introducer may a cross section that is larger than an inner diameter of the guide member 1312.

In some embodiments, the access devices and the systems may further include a sealing device configured to close the hole or channel made by the procedure. In some embodiments, upon completion of the desired procedure, the access port may be closed as described herein and all or parts the heart access device may be withdrawn. The sealing device may include an elongated section. The sealing device may be a plug.

In some embodiments, the sealing device may be configured to be a port for further procedures. In some embodiments, the port may be further configured to be attached to a sealing device delivery device, such as a sealing device introducer. In some embodiments, the sealing device may include a radiopaque marker. The radiopaque marker may be configured to show the sealing on a medical imaging device for later procedures. The medical imaging device may include but is not limited to X-ray, MM and CT. In some embodiments, the radiopaque marker may be a balloon provided at one of the sealing device. The balloon may be capable of being expanded after implantation of the plug.

In some embodiments, the sealing device may further include at least one sensor configured to monitor the heart. For example, the cardiac conduction currents in the myocardium may be monitored.

In some embodiments, the sealing device may be one material. In other embodiments, the plug may be constructed or made of different materials. The sealing device may be constructed or made of a biocompatible material that expands upon insertion. The sealing device may be constructed or made of a dehydrated biocompatible material that expands upon hydration or exposure to biological fluids. The sealing device may be constructed or made of a polymer or material that has shape memory characteristics.

In some embodiments, the sealing device may include a base. The base may be configured to be removably attached to a delivery device, such as a sealing device introducer. The base may include an opening along all or part of the height (perpendicular to the diameter) to communicate with a delivery device. The base may be constructed or made of a biocompatible material, such as Teflon.

Figure 16A:
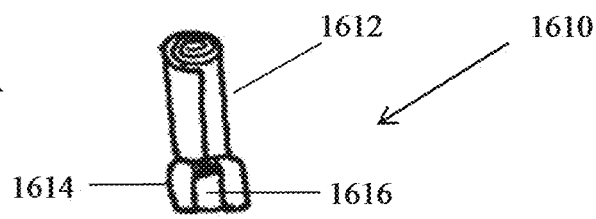
FIGS. 16A-16D show sealing devices according to embodiments.

FIGS. 16(A)-(D) show examples of different sealing devices. FIG. 16(A) shows an example of a sealing device 1610 composed of a wound bioabsorbable material 1612. The bioabsorable material may have a hollow interior or center so as to promote the formation of scar tissue by allowing more absorption of the tissue and blood. The sealing device 1610 may include a base 1614 having an opening 1616.

Figure 16B:
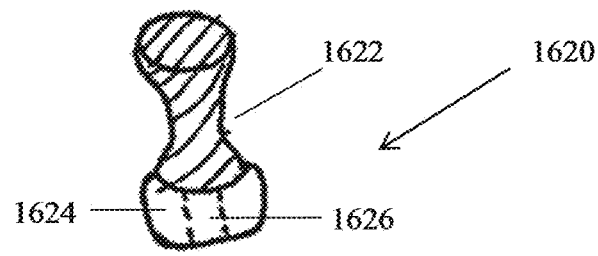

FIG. 16(B) shows an example of a sealing device 1620 of a pre-formed hydrophilic material 1622. The hydrophilic material 1622 may be of any shape. The sealing device 1620 may include a base 1624 having an opening 1626.

Figure 16C:
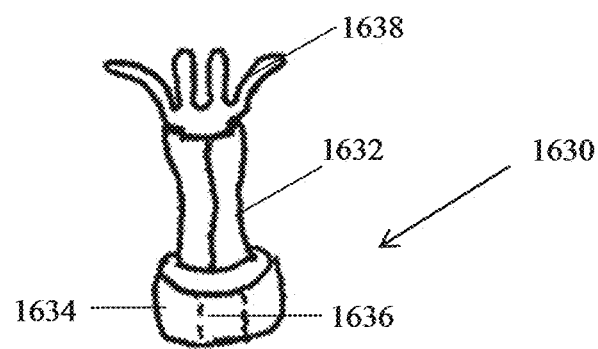

FIG. 16(C) shows another example of a sealing device 1630 of a bioabsorbable material 1632. The material may be wound as shown in, for example, FIG. 16(*a*). The sealing device 1630 may further include one or more than one extending member 1638 configured to contact a surface of the tissue so as to promote the flow of biological fluid and formation of tissue. The extending members 1638 may be flexible. The sealing device 1630 may include a base 1634 having an opening 1636.

Figure 16D:
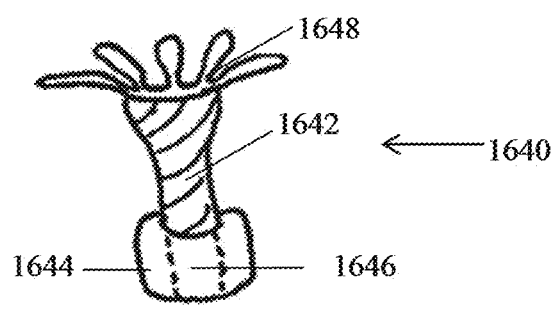

FIG. 16(D) shows another example of a sealing device 1640 of multiple materials. The sealing device 1640 may include an elongated section 1642 constructed or made of a pre-formed hydrophilic material. The sealing device 1640 may further include a clip section 1648 constructed or made of a memory shape alloy, such as Nitinol. The clip section 1648 may include more than one extending member configured to open upon an application of radial force. The clip section 1648 may be configured to anchor the sealing device within the access channel. The sealing device 1630 may include a base 1644 having an opening 1646.

Figure 17:
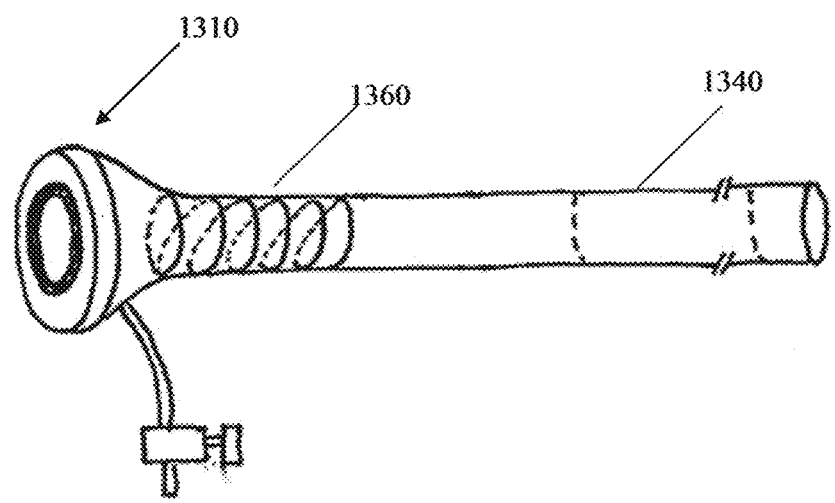
FIG. 17 shows a sheath according to embodiments.

In some embodiments, the sheath may further include a mechanism to promote linear movement of the sheath with respect to a device within its interior bore or channel. In some embodiments, a sheath may include internal threads 1360, as shown in FIG. 17. The internal threads 1360 may be disposed adjacent to the proximal or first end 1310. The internal threads 1360 may be configured or structured to cause the sheath to move distally when a corresponding device engages the internal threads. In some embodiments, the internal threads may be female threads. The mechanism may also be configured to gauge the location of the corresponding device with respect to the sheath and the access channel.

The corresponding device may be an introducer. In some embodiments, the introducer may be configured to deliver energy like the introducer shown in FIG. 12. In other embodiments, the introducer may be configured to deliver and anchor a sealing device in the access channel in the tissue.

Figure 18:
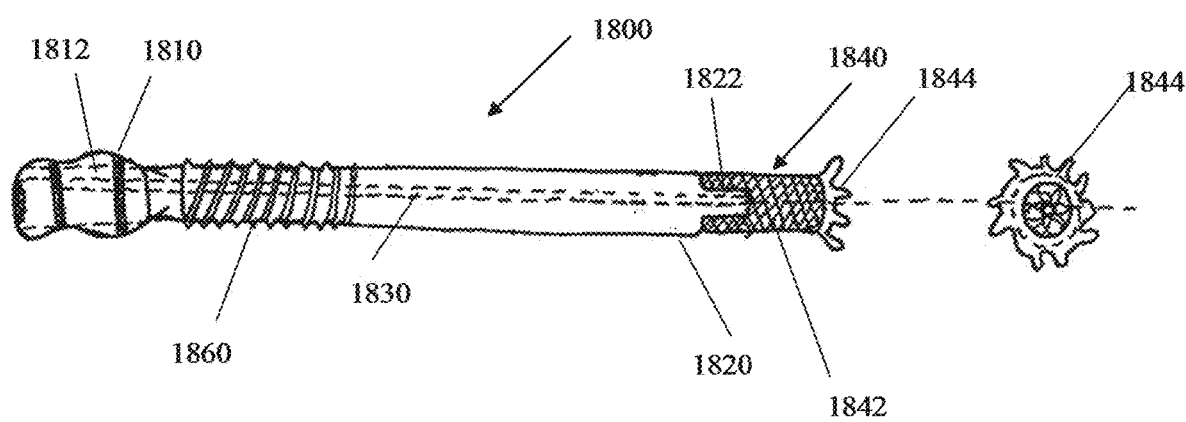
FIG. 18 shows a sealing device introducer according to embodiments.

FIG. 18 shows a sealing device introducer 1800 according to embodiments. In some embodiments, the introducer 1800 may include a first end 1810 and an opposing, second end 1820 (also referred to as proximal and distal ends, respectively), as shown in FIG. 12. In some embodiments, the introducer 1800 may have the same or different diameters along the length (between the first end 1810 and the second end 1820).

In some embodiments, the proximal or first end 1810 may include a guide member 1812. The guide member 1812 may include an entrance to the interior bore or channel 1830. The guide member 1812 may have a larger diameter than the diameter of interior channel or bore the sheath configured to receive the introducer 1800. The guide member 1812 may prevent the introducer from moving further within a sheath. The guide member 1812 may also be configured to form a tight seal with the sheath so as to prevent blood leakage.

In some embodiments, the introducer 1800 may include an inner bore or channel 1830. In some embodiments, the channel 1830 may be along the entire length of the introducer. In other embodiments, the channel 1830 may be along a portion of the entire length of the introducer. In some embodiments, the channel 1830 may begin or have an entrance at the first end 1810. The guide member 1812 may also include an inner channel or bore that corresponds to the channel 1830.

In some embodiments, the introducer 1800 may include a release mechanism configured to release a sealing device 1840 disposed at the distal or second end 1820. The introducer 1800 may include a spring mechanism that is disposed within the channel 1830. The guide member 1812 may be configured to activate the release mechanism, for example, by being depressed.

The second end 1820 may include a holding member 1822 configured to releasably hold a sealing device 1840. The holding member 1822 may be configured to releasably hold and mate a base of the sealing device. In some embodiments, the holding member 1822 may be a protruding member that corresponds to the opening provided in the base as shown in FIGS. 16(A)-16(D).

The sealing device 1840 is not limited to the sealing device shown and may be any sealing device including those described herein. The sealing device 1840 may include an elongated section 1842 constructed or made of a pre-formed hydrophilic material and a clip section 1844 constructed or made of a memory shape alloy, such as Nitinol. The clip section 1844 may include more than one extending member configured to open upon an application of radial force (i.e., being released). The clip section 1844 may be configured to anchor the sealing device within the access channel.

In some embodiments, the sealing device introducer may further include a mechanism to promote linear movement of the sheath with respect to the introducer. The mechanism may also be configured or structured to gauge the location of the introducer with respect to the sheath and the access channel.

In some embodiments, the introducer may include external threads 1860. The internal threads 1860 may be disposed adjacent to the proximally end 1810. The threads 1860 may be configured to cause the sheath to move away from the access channel (proximally) when the threads 1860 engage the internal threads 1360 of the sheath 1300. The threads 1860 may be complimentary to the threads 1360 of the sheath 1300. In some embodiments, the threads 1860 may be male threads. This mechanism may be configured to allow removal of the sheath and introducer after the plug is released and anchored into the channel.

In some embodiments, the access devices and the systems may be configured to deliver a tissue-stabilizing composition before or after the access device is properly positioned. The introducer may be configured to receive a tissue-stabilizing composition delivery device configured to deliver a tissue-stabilizing composition into, around, or adjacent to the tissue. The tissue-stabilizing composition may be a heat shapeable biomaterial formulated for in vivo administration in an area surrounding an access port or channel. The tissue-stabilizing composition is not limited to those described herein.

In some embodiments, the access devices and the systems may include a tissue-stabilizing composition delivery device. In some embodiments, the tissue-stabilizing composition delivery device may be a needle. The needle may have one or more than one opening configured to deliver the tissue-stabilizing composition. In further embodiments, the sheath may include a plurality of ports on the surface near the distal end to deliver the tissue-stabilizing composition into, around or adjacent to the surrounding tissue.

In some embodiments, all or at least one part of the heart access device may be configured to remain in the heart. In some embodiments, all or at least one part of the heart access device may be bioabsorbable. In other embodiments, all or parts of the heart access device may be configured to be removed from the heart.

In some embodiments, the access device may further include one or more sensors. The sensors may be provided on a surface of the access device. In some embodiments, the sheath may include at least one temperature sensors configured to measure the tissue temperature. The temperature sensor(s) may be provided on the surface of the sheath on the end configured to be inserted into the tissue to be heated.

Energy Transduction

In some embodiments, the systems, devices, and methods may provide energy-transducing elements configured or structured to apply energy to surrounding tissue and/or a heat shapeable biomaterial. In certain embodiments, the energy delivered may be below a temperature sufficient for effecting crosslinking of the biomaterial and surrounding tissue. In some embodiments, the energy may be delivered to the tissue needed for treatment at or adjacent a tissue structure. The energy may heat surrounding tissue and/or shapeable biomaterial or cause the temperature of the surrounding tissue and/or shapeable biomaterial to rise. Examples of energy sources and energy-transducing elements configured or structured for energy transduction are described herein.

In other embodiments, the energy being delivered reduces the temperature of the surrounding tissue. In these embodiments, the sheath is inserted into the tissue and a cryo-probe, capable of reducing the temperature of the tissue is provided.

Moderate heat is known to tighten and shrink the collagen tissue as illustrated in U.S. Pat. Nos. 5,456,662 and 5,546,954. It is also clinically verified that thermal energy is capable of denaturing the tissue and modulating the collagenous molecules in such a way that treated tissue becomes more resilient ("The Next Wave in Minimally Invasive Surgery" MD & DI pp. 36-44, August 1998). The general method according to embodiments applies appropriate heat to the tissues, and causes them to shrink and tighten. It may be performed in a minimal invasive fashion, which is often less traumatic than surgical procedures and may be the only alternative method, wherein other procedures are unsafe or ineffective. Ablative treatment devices have an advantage because of the use of a therapeutic energy that is rapidly dissipated and reduced to a non-destructive level by conduction and convection, to other natural processes.

Radiofrequency (RF) therapeutic protocol has been proven to be highly effective when used by electrophysiologists for the treatment of tachycardia, atrial flutter and atrial fibrillation; by neurosurgeons for the treatment of Parkinson's disease; by otolaryngologist for clearing airway obstruction and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. Radiofrequency energy, when coupled with a temperature control mechanism, can be supplied precisely to the device-to-tissue contact site to obtain the desired temperature for treating a tissue or for effecting the desired shrinking of the host collagen or injected biomaterial adapted to immobilize the biomaterial in place.

Edwards et al. in U.S. Pat. No. 6,258,087 describes an expandable electrode assembly comprising a support basket formed from an array of spines for forming lesions to treat dysfunction in sphincters. Electrodes carried by the spines are intended to penetrate the tissue region upon expansion of the basket. Similarly, Tu in U.S. Pat. No. 6,267,781 teaches an ablation device for treating valvular annulus or valvular organ structure of a patient, comprising a flexible elongate tubular shaft having a deployable spiral wire electrode at its distal end adapted to contact/penetrate the tissue to be treated and to apply high frequency energy to the tissue for therapeutic purposes. Tu et al. in U.S. Pat. No. 6,283,962 discloses a medical ablation device system for treating valvular annulus wherein an elongate tubular element comprises an electrode disposed at its distal section that is extendible from an opening at one side of the tubular element, the energy generator, and means for generating rotational sweeping force at the distal section of the tubular element to effect the heat treatment and the rotational sweeping massage therapy for target tissues. U.S. Pat. No. 5,980,563 describes certain ablation methods and apparatus for treating atherosclerosis. Similarly, U.S. Pat. No. 6,882,885 to Solarant describes certain heating methods for tissue contraction. U.S. Pat. Nos. 6,485,489 and 6,306,133 describe certain ablation catheter systems for applying heat to an annulus defect to shrink or tighten the tissue.

Ultrasound is cyclic sound pressure with a frequency greater than the upper limit of human hearing. Although this limit varies from person to person, it is approximately 20 kilohertz (20,000 hertz) in healthy, young adults and thus, 20 kHz serves as a useful lower limit in describing ultrasound. The production of ultrasound is used in many different fields, typically to penetrate a medium and measure the reflection signature or supply focused energy. The reflection signature can reveal details about the inner structure of the medium, a property also used by animals such as bats for hunting. The most well-known application of ultrasound is its use in sonography to produce pictures of fetuses in the human womb. There are a vast number of other applications as well. Ultrasound energy has two potential physiological effects: it enhances inflammatory response and it can heat soft tissue. Ultrasound energy produces a mechanical pressure wave through soft tissue. This pressure wave may cause microscopic bubbles in living tissues and distortion of the cell membrane, influencing ion fluxes and intracellular activity. When ultrasound enters the body, it causes molecular friction and heats the tissues slightly. This effect is typically very minor as normal tissue perfusion dissipates most of the heat, but with high intensity, it can also cause small pockets of gas in body fluids or tissues to expand and contract/collapse in a phenomenon called cavitation. Ultrasound has been used successfully to shrink the mitral valve annulus (see ReCor Medical press release, 2010).

Another mechanism that may be used to heat tissue in a localized for to increase stability is microwave radiation. Typically, thermal coagulation of tissue involves the use of microwaves to induce an ultra-high-speed (2450 MHz) alternating electric field, causing the rotation of water molecules. Although the use of microwaves for tissue ablation is not new, the majority of the clinical experience with this technique to ablate liver tumors comes from Japan. Percutaneous microwave ablation was first used as an adjunct to liver biopsy in 1986, but it has since been used for hepatic tumor ablation. As with RF ablation, microwave ablation involves placement of a needle electrode directly into the target tissue.

Tissue-Stabilizing Compositions

Moderate heat is known to tighten and shrink the collagen tissue. The same shrinking/tightening techniques may also be applicable to stabilize injected biomaterial that allow stabilization of the tissue surrounding the apical access device wherein the injectable biomaterial is suitable for penetration and heat-initiated shrinking/tightening. The general method applies appropriate heat to the tissues, and causes them to shrink and tighten. It may be performed in a minimal invasive fashion, which is often less traumatic than surgical procedures and may be the only alternative method, wherein other procedures are unsafe or ineffective. Ablative treatment devices may have an advantage because of the use of a therapeutic energy that is rapidly dissipated and reduced to a non-destructive level by conduction and convection, to other natural processes.

A variety of materials may be injected to improve the stability of the tissue or improve the sensitivity of the tissue to the heat treatment. In some embodiments, the composition that is administered is a gelatin-resorcinol-formaldehyde (GRF) glue (see Nguyen, et al. (1999) *Eur J Cardiothorac Surg* 15:496-500). In other embodiments, the material is a gelatin-resorcinol-formaldehyde-glutaraldehyde (GRFG) glue (see Nomori and Horio (1997) *Ann Thorac Surg* 1997 63:352-355). In another embodiment, the composition or compound is a gluteraldehyde/bovine serum albumin solution. The material may be a BioGlue Surgical Adhesive consisting of two components, a 10% glutaraldehyde solution and a 45% bovine serum albumin solution, which are kept separate until the time of application (see BioGlue® Product Information. CryoLife, Inc, Kennesaw, GA, 1998).

In some embodiments, the material may be a biomolecular material comprising at least one biomolecule which has been mixed at high concentration with an aqueous solvent. The biomolecule(s) may be typically proteinaceous but it is envisaged that other naturally occurring biomolecules could be used as alternatives. Further, analogues of biological, biodegradable polypeptides may also be used. Analogues of biological, biodegradable polypeptides useful in the solders of the disclosure include synthetic polypeptides and other molecules capable of forming the material but which do not cause adverse reaction in the tissue undergoing repair. Examples of suitable proteins include albumins, collagen, fibrinogen and elastin. Suitable proteins are typically those which can be cross-linked to form a matrix and which can be resorbed by the body. Where combinations of proteins are used it is envisaged that those combinations will be of proteins having similar denaturation temperatures. An example is the combination of albumin and collagen. Use of different albumins is contemplated including bovine, horse, human, rat, ovine and rabbit albumin. The choice of a particular albumin may be made to reduce immunological reaction in the patient to the material. It is envisaged that there will be circumstances where the albumin used may be chosen to match the patient's blood type and possibly even more specifically with regard to histocompatibility markers of the patient in question. The solvent may be typically water but other aqueous solvents including saline may be used provided that any salt etc. present does not adversely affect the material upon denaturation. Various adjuvants may be added to the material to promote rapid or more complete tissue healing, e.g. fibrinogen (for blood vessels), growth factors, sodium hyaluronate (for improved viscous handling and possibly better healing), hormones, and/or anticoagulants, such as heparin. Various fibrous materials may be added to the material to improve the strength (e.g. collagen or polytetrafluoroethylene fiber (which is sold under the brand names goretex and teflon) or ceramic fibers). The fibers may typically be biocompatible polymers.

There are a variety of collagen-based compositions available that may be used in the present disclosure. These may include type I and type III injectable human collagen product derived from human sources (containing type I and type III collagen in a proportion of 44:56) (see e.g. Liu, et al. (2005) *Semin Plast Surg.* 19: 241-250). Similarly, Bovine injectable collagen (Zyderm I®, Zyderm II®, and Zyplast® collagen implants; Inamed Corporation, Santa Barbara, Calif.) are readily available. U.S. Pat. No. 4,837,285 describes certain collagen-based compositions for augmenting soft tissue, wound dressings, implants, injectable formulations or other drug delivery systems, comprising resorbable collagen matrix beads. U.S. Pat. No. 6,110,212 describes the use of certain elastin-based biomaterials for tissue repair or replacement.

Fibrinogen compositions are also readily available. These may include RiaSTAP™, a heat-treated, lyophilized fibrinogen (coagulation factor I) powder made from pooled human plasma. This composition may include fibrinogen, human albumin, L-arginine hydrochloride, sodium chloride and sodium citrate. In addition, Oss-Ronen and Seliktat described certain polymer-conjugated albumin and fibrinogen composite hydrogels in which serum albumin was conjugated to poly-(ethylene glycol) (PEG) and cross-linked to form mono-PEGylated albumin hydrogels.

Albumin compositions have also been used for tissue repair. In some instances, the albumin is stabilized with additional compounds or compositions, such as genepin to increase crosslinking. In addition, chitosan has been used to improve the malleability of albumin compositions, as well as to bind to collagen. Chitosan has also been modified with lactobionic acid and p-azidebenzoic acid, which can be cross-linked with UV light. U.S. Pat. No. 5,292,362 describes certain tissue bonding materials including albumins and fibrinogens.

Biomaterials based upon elastin and elastin-derived molecules are increasingly investigated for their application in tissue engineering. This interest is fuelled by the remarkable properties of this structural protein, such as elasticity, self-assembly, long-term stability, and biological activity. Elastin can be applied in biomaterials in various forms, including insoluble elastin fibres, hydrolysed soluble elastin, recombinant tropoelastin (fragments), repeats of synthetic peptide sequences and as block copolymers of elastin, possibly in combination with other (bio) polymers. In this review, the properties of various elastin-based materials will be discussed, and their current and future applications evaluated. In certain embodiments, tropoelastin monomers and lysyl oxidase can be prepared and suspended an aqueous solution (e.g., water or saline) or in a lyophilized form and kept separate from each other until right before use. U.S. Pat. No. 6,110,212 describes certain elastin-based materials that can be useful for stents. These materials may also be useful in the present disclosure.

Other compositions known in the art that allow strengthening of the tissue can also be used.

Detailed Methods of Providing Stable Access to a Heart Chamber & Delivering a Prosthesis In some embodiments of the present disclosure, methods for providing a stable access to a heart chamber for medical procedures are provided. In further embodiments, methods for delivering a prosthesis to a target site in or near a heart are provided.

In some embodiments of the present disclosure, a method of providing access to a target site in or near a heart is provided. The method includes (i) providing an access channel into the chamber; (ii) providing an energy-transducing element configured to provide heat to tissue surrounding the access channel; and (iii) applying energy to the tissue.

In some embodiments, the methods may include providing an access channel into the chamber. In certain embodiments, the steps of providing an access channel may include introducing a heart access device according to embodiments into a heart chamber. In some embodiments, the heart access device may be introduced by any known method. In some embodiments, the step of introducing a heart access device described herein may include the steps of the method shown and described with respect to FIGS. 2(A)-(D).

In some embodiments, the access channel may be disposed at or near the apex of the heart. In other embodiments, the access channel may at other areas of the heart.

Figure 5:
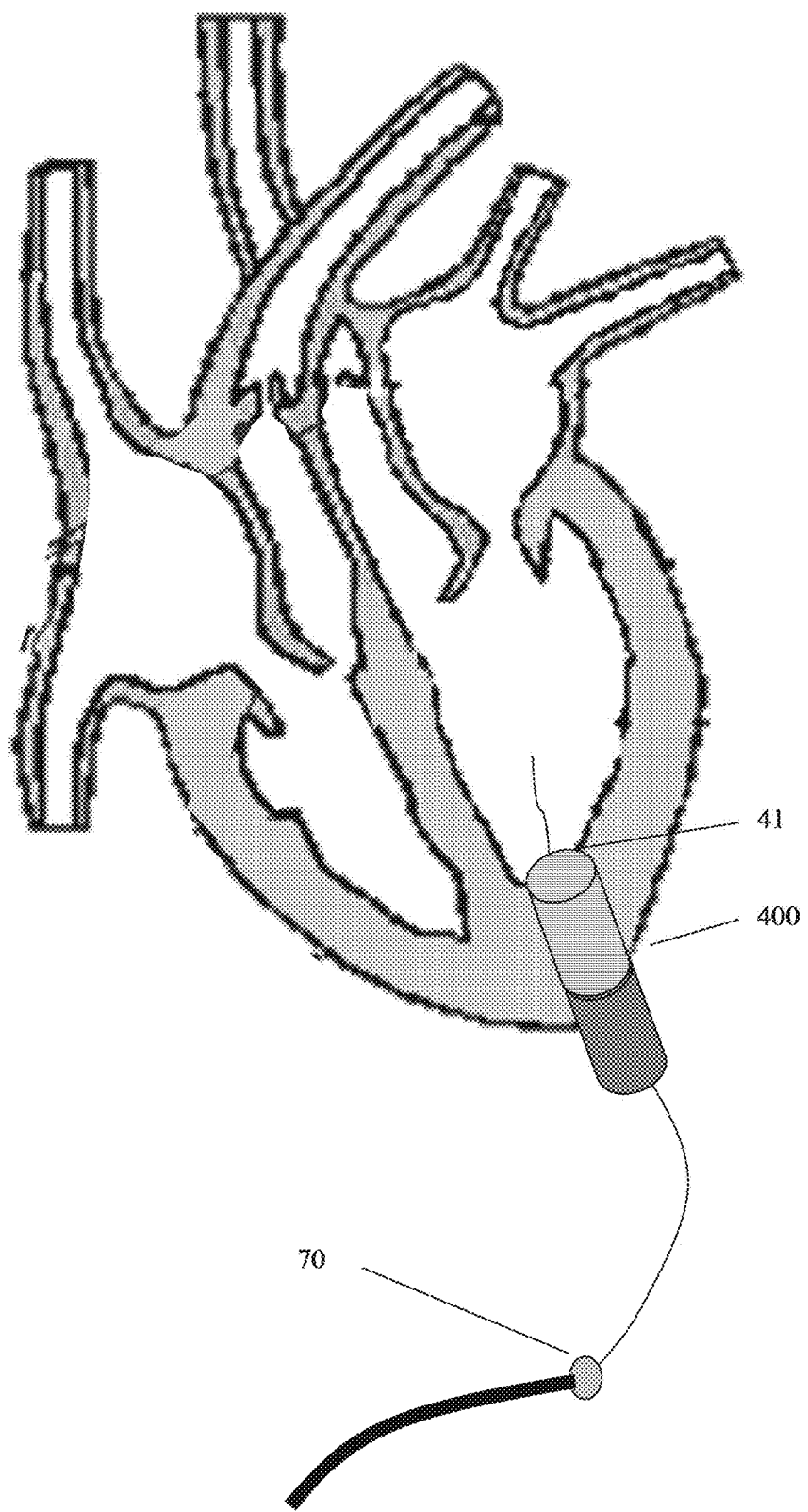
FIG. 5 shows the insertion of a heart access device into the tissue of the heart according to embodiments.

In some embodiments, the steps of introducing the heart access device 400 may include inserting the sheath 40 into the apex of the heart and positioning the sleeve 45 inside the heart tissue (see FIG. 5).

Figure 6:
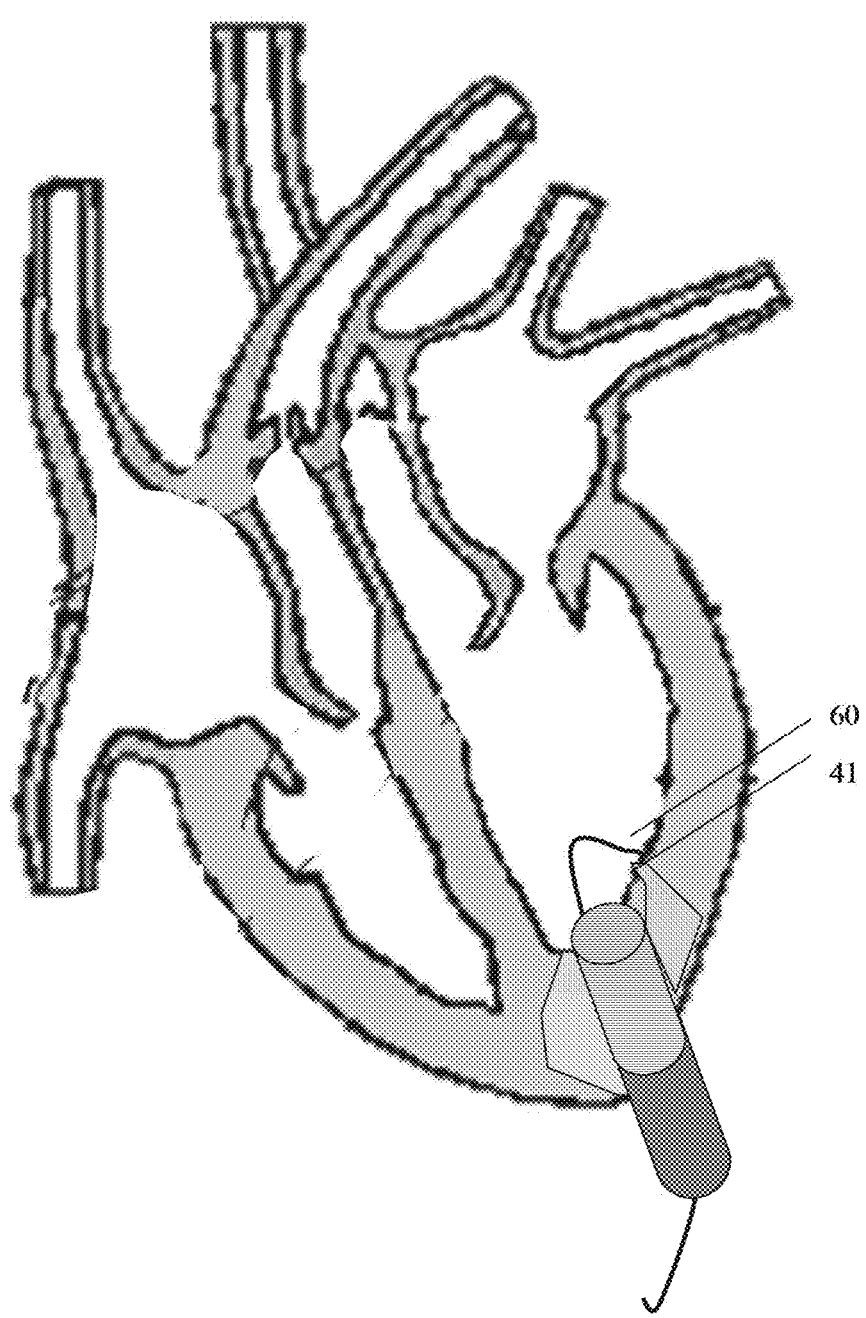
FIG. 6 shows a detail of injection of a tissue-stabilizing composition into the tissue surrounding the access port (also referred to as "access channel").
Figure 7:
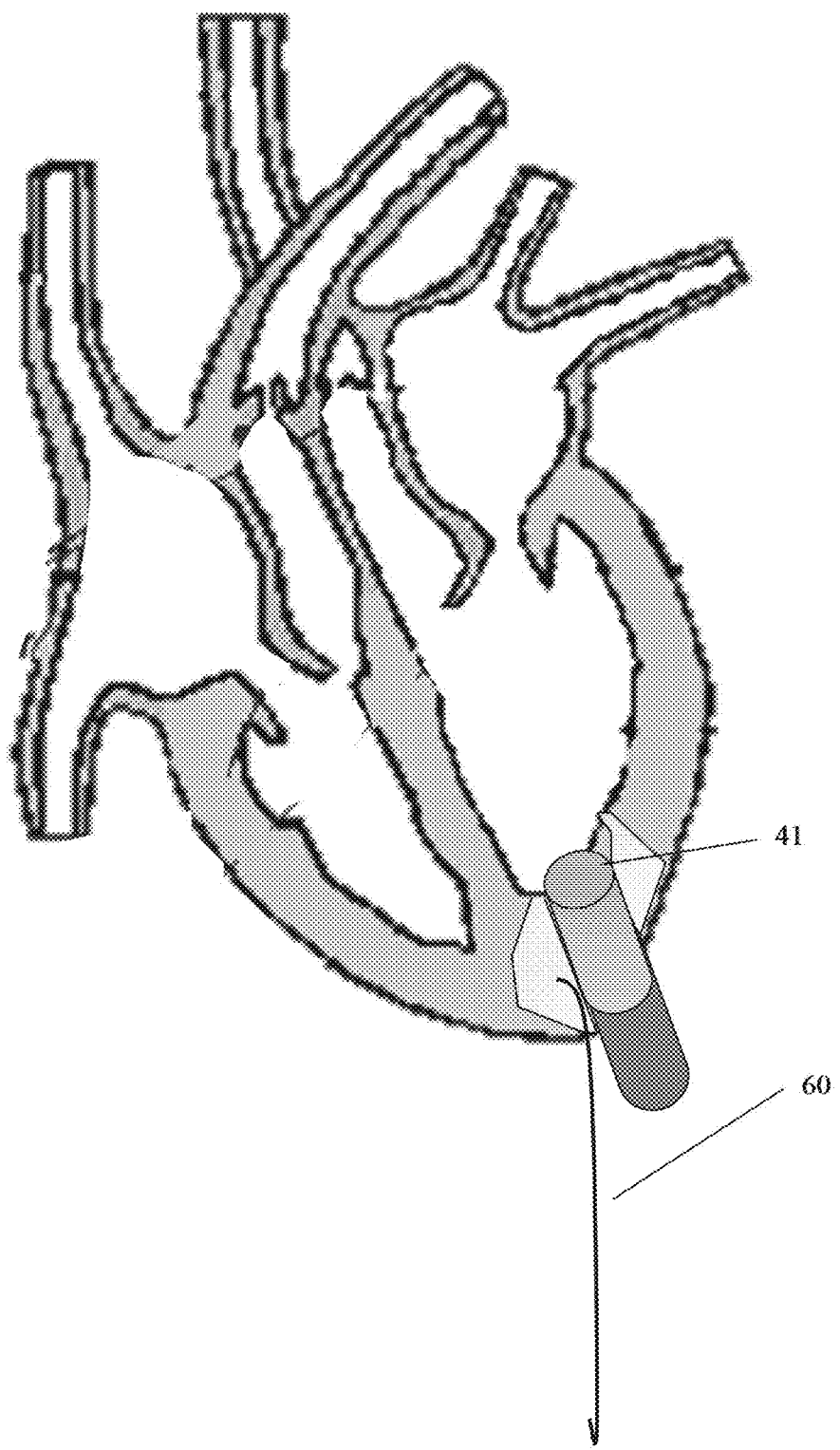
FIG. 7 shows a different embodiment detail of injection of a tissue-stabilizing composition into the tissue surrounding the access port.

In certain embodiments, in particular in patients in need of additional stabilization of heart tissue such as the elderly (above 65), the method may optionally include a step of administering or delivering a tissue-stabilizing composition. The tissue-stabilizing composition may be administered by threading a needle 60 or other device sufficient to administer a tissue-stabilizing composition through (FIG. 6) or alongside (FIG. 7) the sheath. In some embodiments, a tissue-stabilizing composition may be administered into the tissue surrounding the sheath as shown in FIG. 6. In other embodiments, a tissue-stabilizing composition may be administered to the tissue surrounding the access port as shown in FIG. 7. In some embodiments, the tissue-stabilizing composition may be a heat shapeable biomaterial formulated for in vivo administration in an area surrounding an access port. The heat shapeable biomaterial may be formulated for in vivo administration in an area surrounding an access port.

In some embodiments, the methods may further include the steps of providing an energy source 70 and applying energy. In some embodiments, the energy source may be configured to provide heat to tissue surrounding the access channel and energy may be applied to the tissue. Energy may be delivered to the tissue at a level sufficient to increase the structural stability of the tissue. In some embodiments, the energy source 70 may be provided by an introducer.

In other embodiments, the energy source may be configured to additionally or alternatively heat an injected tissue-stabilizing composition. The tissue-stabilizing composition may have been injected into, around, or adjacent to the tissue. In some embodiments, the methods may include applying heat sufficient to shape the biomaterial and immobilize the biomaterial at about the access port after injection. In certain embodiments, the heat delivered may be below a temperature sufficient for effecting crosslinking of the biomaterial and surrounding tissue.

The methods may further include a step to anchor the access device so that cardiac procedures may be performed. In some embodiments, a balloon may be used to position the access system. In other embodiments, another positioning tool may be used. In some embodiments, the fasteners may be used to anchor the access device. The fasteners may include but are not limited to anchors, stent expansion, screws or biological glues. As shown in FIG. 8, after stabilization of the tissue, an expandable balloon may be advanced over the guide wire into the cardiac chamber, illustratively in the form of balloon 80. The balloon 80 may be advanced through the sheath and expanded into the ventricular space.

When inflated, as depicted in FIG. 8, the balloon may generally be in the form of a surface of revolution about a central axis coincident with proximal-to-distal axis of the catheter. The diameter of the balloon may typically be about 20 mm and may usually be formed from a polymer such as nylon with a wall thickness of about 8 microns to about 30 microns.

The balloon may then pulled outwards to move the sleeve into a position in which the distal end 41 of the sleeve 45 is in line or coincident with the interior of the tissue 82. The balloon may then deflated and withdrawn. When deflated, the balloon may collapse inwardly to form a relatively small diameter structure. The balloon may be fabricated by blow-molding using techniques that are known in the art. This positioning of the sheath may be accomplished either before or after the tissue strengthening procedure.

The sleeve 45 may then be anchored into the tissue using any biocompatible fasteners. The fasteners may include but are not limited to anchors, stent expansion, screws or biological glues.

After the access system has been stabilized, an interventional procedure may then be performed by insertion of instruments through the sheath. In some embodiments, this may include implanting or delivering a prosthesis. The prosthesis may be any known cardiac prosthesis. The prosthesis may include but are not limited to replacement or repair valve devices. In some embodiments, after a stable access is provided, the methods may further include steps to deliver a prosthesis to a target site in or near a heart. The methods may further iv) introducing a delivery system into the heart through an access channel, wherein a prosthesis is disposed on the delivery member attached to the delivery system; (v) advancing the prosthesis to the target site; and (vi) disengaging the prosthesis from the delivery member at the target site for implantation.

After completion of the procedure, the sealing device 90 may be inserted into the sheath. The sealing device may be a plug. The plug may be typically made of a material that expands upon insertion, for example, a dehydrated material that expands upon hydration. The surface of the plug facing the cardiac chamber may be typically made of a polymer material that encourages rapid endothelialization. Normally, endothelial cells (EC) migrate and proliferate to cover denuded areas until confluence is achieved. Although the process of recognition and signaling to determine specific attachment receptor response to attachment sites is incompletely understood, regular availability of attachment sites, more likely than not, would favorably influence attachment and migration. There have been numerous attempts to increase endothelialization of devices such as implanted stents, including covering with a polymeric material (see e.g. U.S. Pat. No. 5,897,911), imparting a diamond-like carbon coating (see e.g. U.S. Pat. No. 5,725,573), covalently binding hydrophobic moieties to a heparin molecule (see e.g. U.S. Pat. No. 5,955,588), coating with a layer of blue to black zirconium oxide or zirconium nitride (see e.g. U.S. Pat. No. 5,649,951), coating with a layer of turbostratic carbon (see e.g. U.S. Pat. No. 5,387,247), coating with a thin layer of a Group VB metal (see e.g. U.S. Pat. No. 5,607,463), imparting a porous coating of titanium or of a titanium alloy, such as Ti—Nb—Zr alloy (see e.g. U.S. Pat. No. 5,690,670), coating with a synthetic or biological, active or inactive agent, such as heparin, endothelium derived growth factor, vascular growth factors, silicone, polyurethane, or polytetrafluoroethylene, (see e.g. U.S. Pat. No. 5,891,507), coating with a silane compound with vinyl functionality, then forming a graft polymer by polymerization with the vinyl groups of the silane compound (see e.g. U.S. Pat. No. 5,782,908), grafting monomers, oligomers or polymers onto a surface using infrared radiation, microwave radiation or high voltage polymerization to impart the property of the monomer, oligomer or polymer (see e.g. U.S. Pat. No. 5,932,299). Any such materials, or others known in the art, may be used to manufacture all or part of the plug to be used in the present disclosure.

Figure 9:
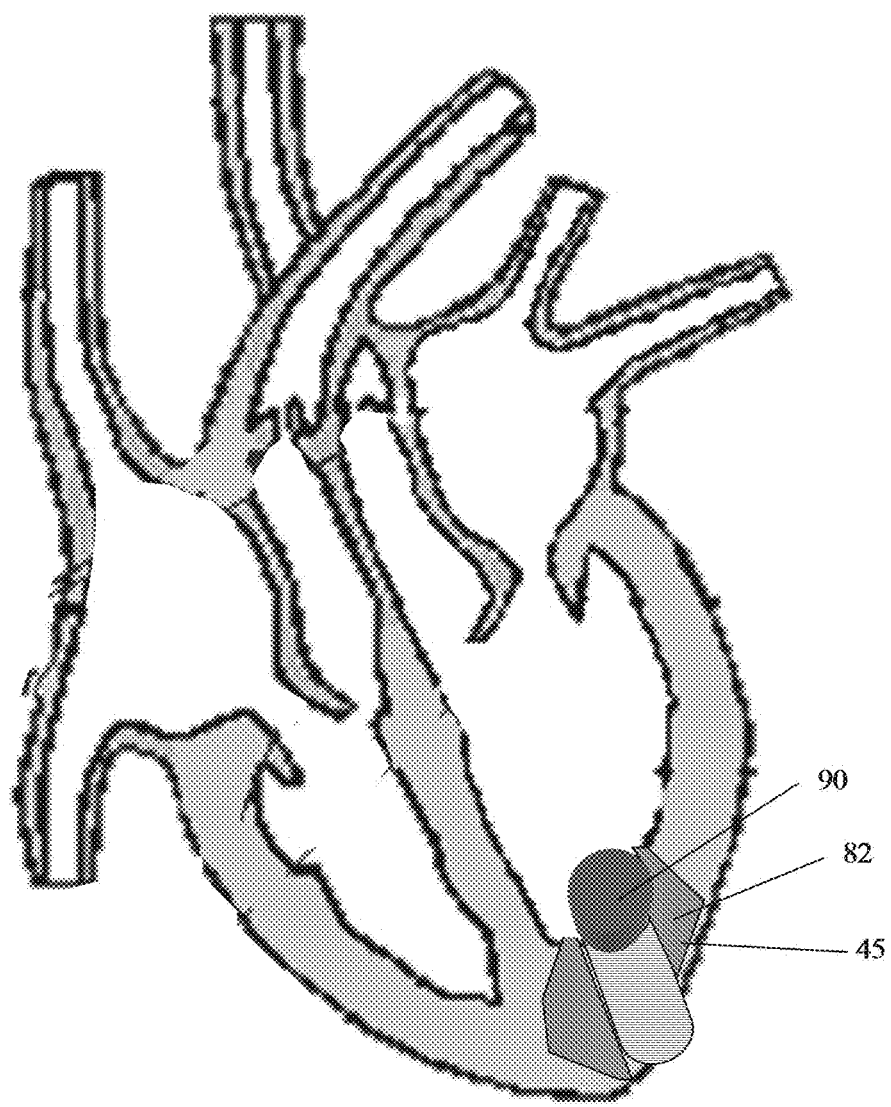
FIG. 9 shows insertion of a sealing to close the access port, and removal of the remainder of the sheath from the sleeve.

After insertion of the plug 90, the sleeve 45 may be removed from the remainder of the sheath 400 and the remainder of the sheath 400 may be withdrawn from the body (see FIG. 9). As shown in FIGS. 10 and 11, typically, the sleeve may be attached by a snap mechanism 1010 to the remainder of the sheath or may be attached via a screwtop mechanism 1110 to the remainder of the sheath. Other mechanisms that may be used to separate the sleeve from the remainder of the sheath are also envisioned herein.

In another embodiment of the disclosure, the sleeve may be removed completely, leaving the sealing device (the plug) in place. In some embodiments, the sealing device (the plug) may be fabricated from a biodegradable material, which may decrease the tendency for infection that is associated with any foreign body left in place.

According to some embodiments, the steps for creating or accessing an access channel may depend on the access device used and type of procedure performed. An example of a minimally invasive method of providing apical access to heart chamber for a medical procedure is shown in FIGS. 19 through 27. The method shown may also be performed percutaneously. FIGS. 28 through 39 show an example of the method being performed on a pig heart.

Figure 19:
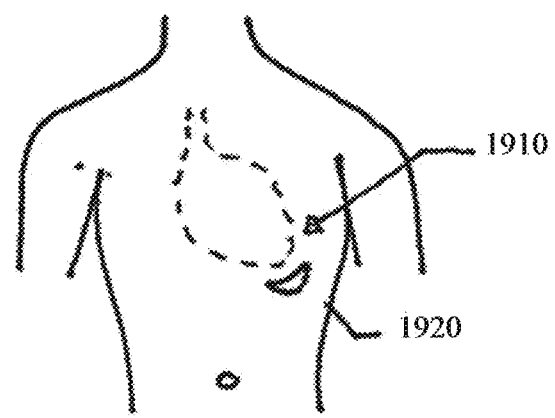
FIG. 19 shows a detail of identifying the location for performing a method according to embodiments.

According to some embodiments, the step of creating the access channel may include identifying the location of apex with medical imaging, such as fluoroscopy or echocardiography. The location of the left-ventricle (LV) apex may be identified. In FIG. 19, the LV apical region 1910 may be located and an incision 1920 may be made.

Figure 20:
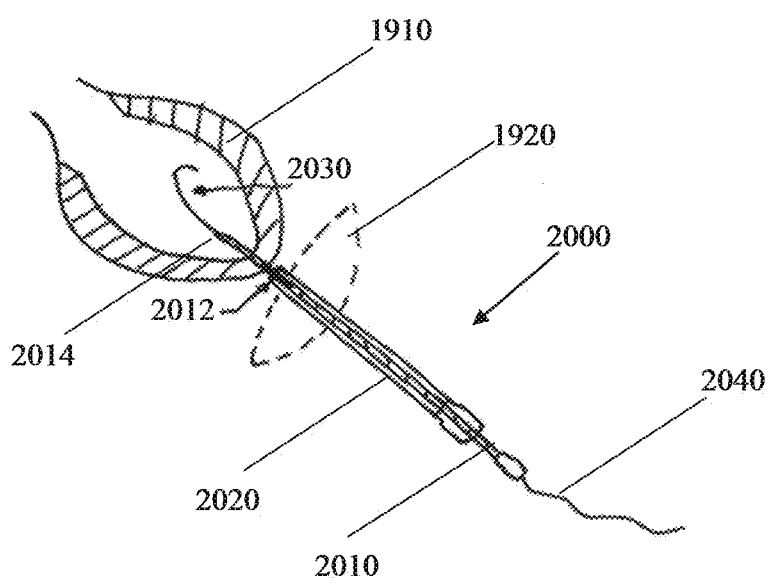
FIG. 20 shows a detail of inserting an access device according to embodiments.
Figure 28:
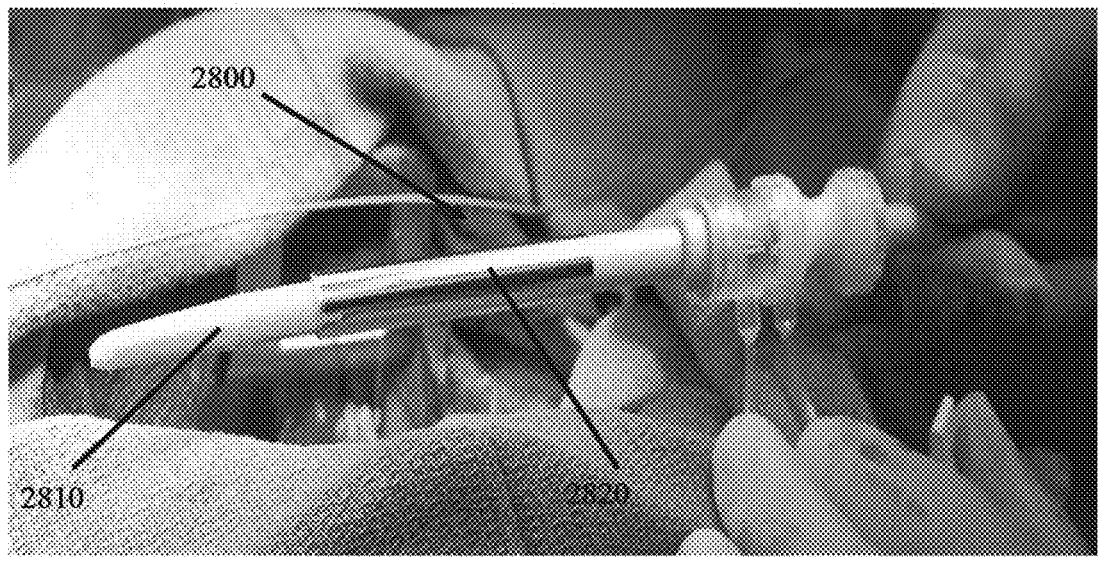
FIG. 28 shows an example of a heart access device according to embodiments.

The step of creating the access channel may further include introducing an access device into the LV region. The access device may include an introducer and a sheath. Example of an access devices are shown in FIGS. 20 and 28. In FIG. 20, the access device 2000 includes an introducer 2010 and a sheath 2020. The introducer 2010 may include energy-transducing components 2012 located close to the distal end 2014. The introducer 2010 may be connected to a power source 2040. The energy source and the energy-transducing components may be according any of the embodiments described herein. In FIG. 28, the access device 2800 includes a sheath 2810 and an introducer 2820.

Figures 29, 30, 31:
FIGS. 29 through 34 show details of the method according to embodiments performed on a pig heart.

The step of introducing an access device to the heart may include positioning and inserting the introducer into the heart. The introducer 2820 may be first positioned in the LV region 2900, as shown in FIG. 28. Next, the introducer 2820 may be inserted and advanced into the LV region 2900, as shown in FIG. 29. The introducer may be guided by a guidewire. The 2820 may be configured to puncture the tissue of the heart, the myocardium, so as to create an access channel in the myocardium. As shown in FIG. 20, the introducer 2010 may be guided by guidewire 2030 into the myocardium.

Figure 21:
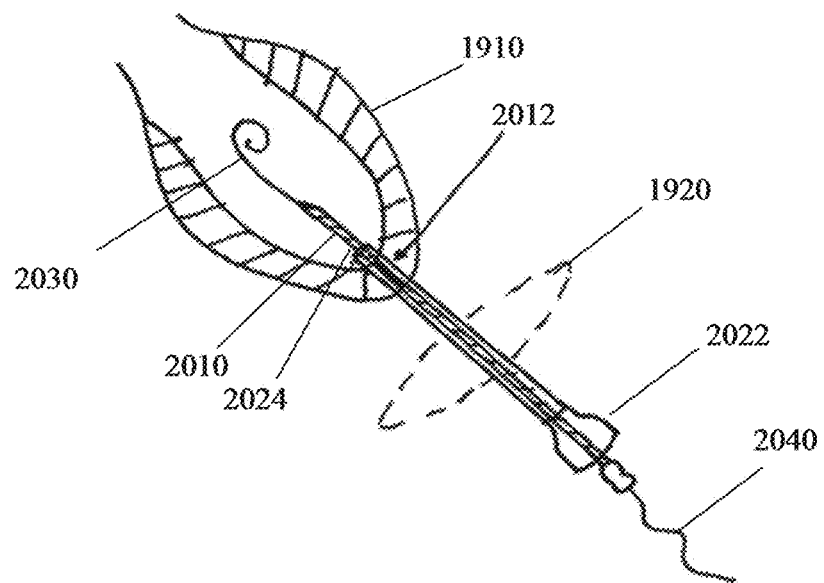
FIG. 21 shows a detail of positioning the access device according to embodiments.

The introducer may be advanced so that the energy-transducing components may be adjacent to or substantially adjacent to the myocardium of the LV region and the distal end 2014 may be located inside a heart chamber. After the introducer is properly positioned in the LV region 1910, the sheath may then be advanced. As shown in FIGS. 20 and 21, the sheath 2020 may be advanced over the introducer 2010 until the distal end 2024 of the sheath 2020 is located within the chamber. In some embodiments, the sheath 2020 may be advanced until the energy dispersing region corresponds to the region of the introducer including the energy-transducing components. FIG. 31 also shows the sheath 2810 being be moved or forwarded along the introducer into the LV region 2900.

Figure 22:
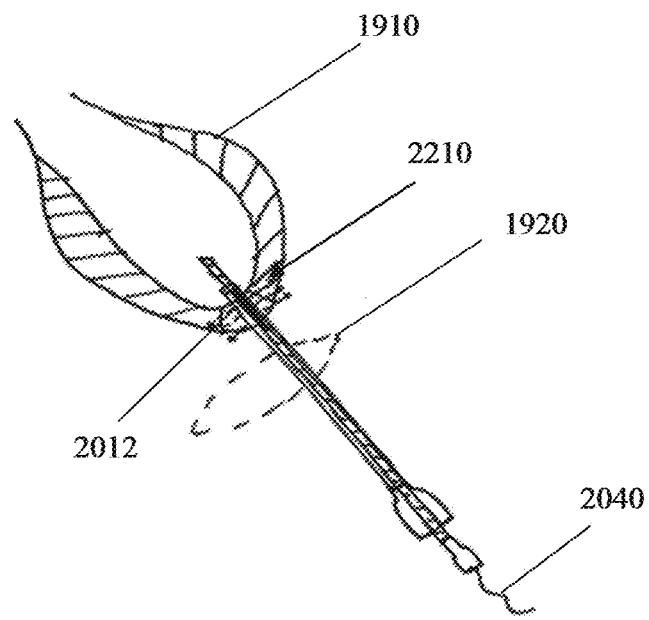
FIG. 22 shows a detail of applying energy to surrounding tissue according to embodiments.
Figures 32, 33, 34:
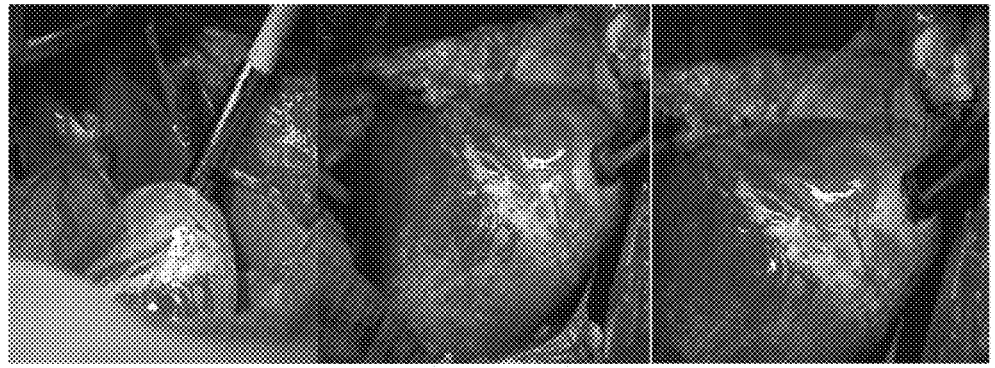

After the sheath and the introducer are properly positioned within the myocardium as shown in for example, FIGS. 22 and 32, the energy may be applied. As shown in FIG. 22, energy 2210 may be dispersed from the energy-transducing components 2012 through the sheath 2020 to the tissue surrounding the access device 2000. The energy-transducing components 2012 may be provided power by a power source 2040. FIG. 33 also shows energy being applied to tissue surrounding the sheath 2810.

Figure 23:
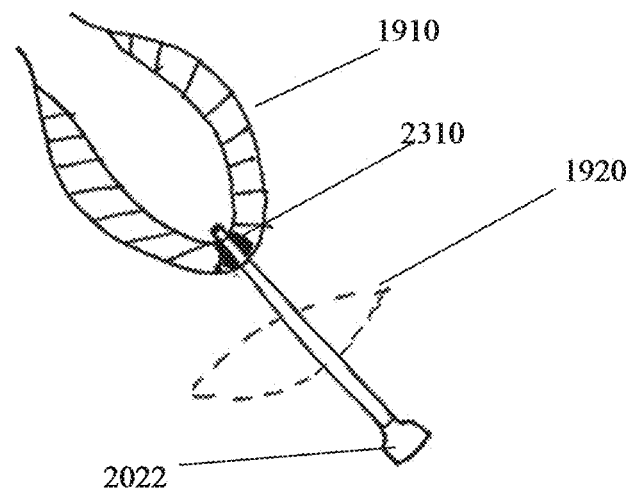
FIG. 23 shows a detail of positioning the sheath to perform medical procedures according to embodiments.

The surrounding tissue 2310 treated by energy strengthens and radially contracts onto the sheath, as shown in FIG. 23. FIG. 34 shows treated tissue. The treated tissue has a change of color around insertion point. After the tissue has been treated, the sheath may remain in place for medical procedure(s). Interventional or diagnostic procedures may be performed through the sheath. The valve 2022 may be closed to restrict blood loss. After the procedures have been performed, a sealing device may be introduced into the access channel.

Figure 24:
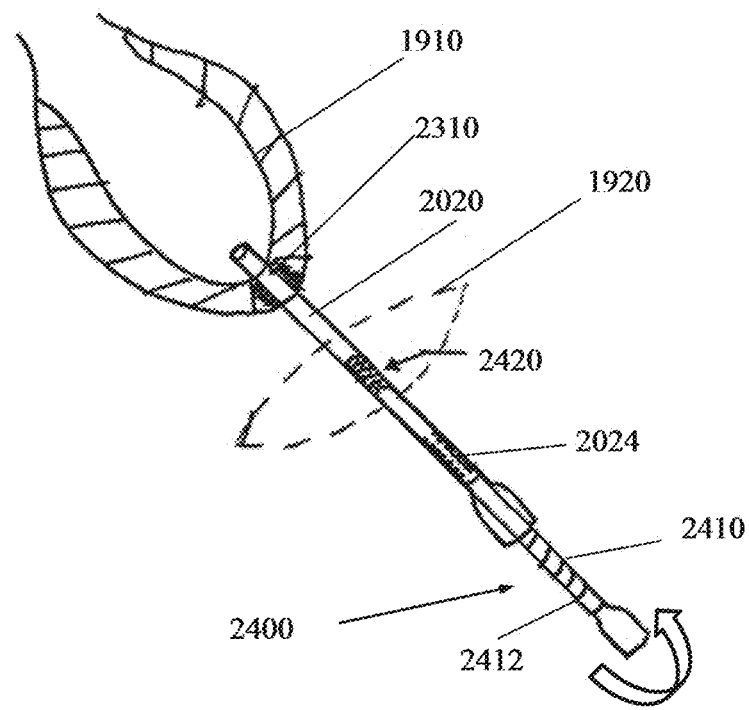
FIG. 24 shows a detail of introducing a sealing device introducer according to embodiments.
Figure 25:
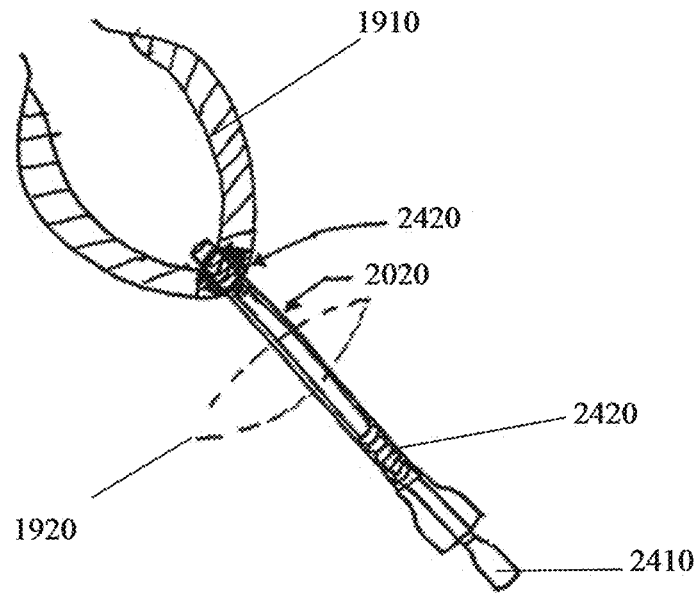
FIG. 25 shows a detail of positioning the sealing device according to embodiments.
Figure 26:
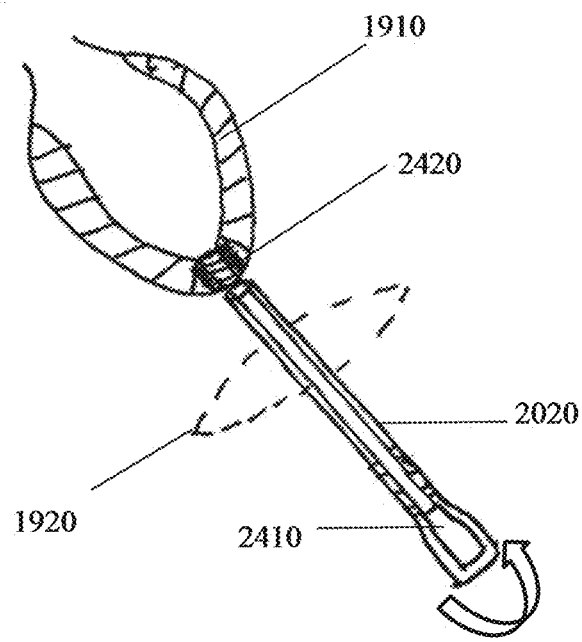
FIG. 26 shows a detail of retracting the access device according to embodiments.

In some embodiments, as shown in FIGS. 24 through 26, a sealing device 2420 may be introduced by a sealing device introducer 2410. The sealing device introducer 2410 may be according to the embodiments described herein. The sealing device introducer 2410 may be inserted into the sheath to position sealing device 2420. The sealing device 2420 may be pushed along and within the sheath by rotating the sealing device introducer 2410, as shown in FIGS. 24 and 25. In some embodiments, the sealing device introducer 2410 may include threads 2412 at the proximal end that are configured to engage corresponding threads 2024 of the sheath 2020. A user may know that the sealing device is properly positioned within the access channel by counting the rotations of the sealing device introducer.

Figure 27:
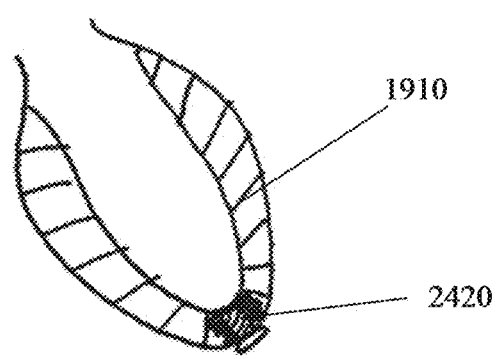
FIG. 27 shows the removal of the access device according to embodiments.
Figure 35:
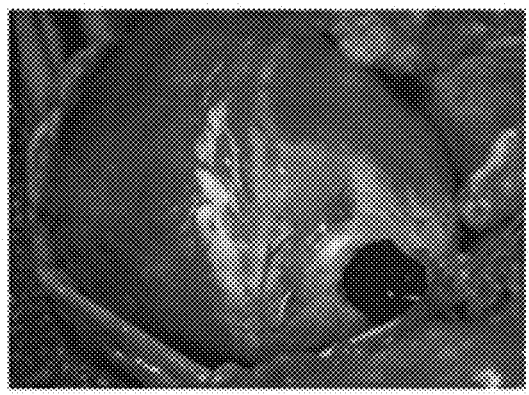
FIGS. 35 through 39 show results of the method shown in FIGS. 29 through 34.

After the sealing device is positioned within the access channel in the myocardium, the sheath may be removed from the access channel. The sheath 2020 may be retracted back with the sealing device introducer 2410 towards the user, as shown in FIG. 26. The sealing device may remain in the myocardium. FIG. 27 shows an example of a sealing device 2420 anchored into the access channel formed in the myocardium. FIG. 35 also shows a sealing device anchored into the access channel.

Figure 36:
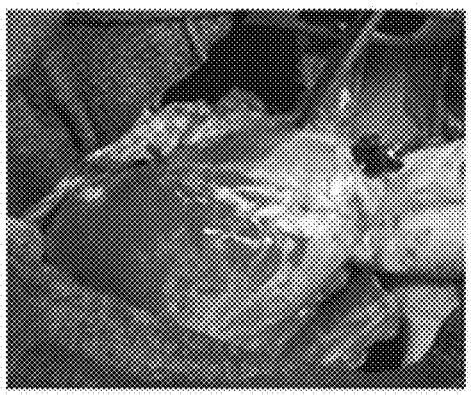
Figures 37, 38, 39:
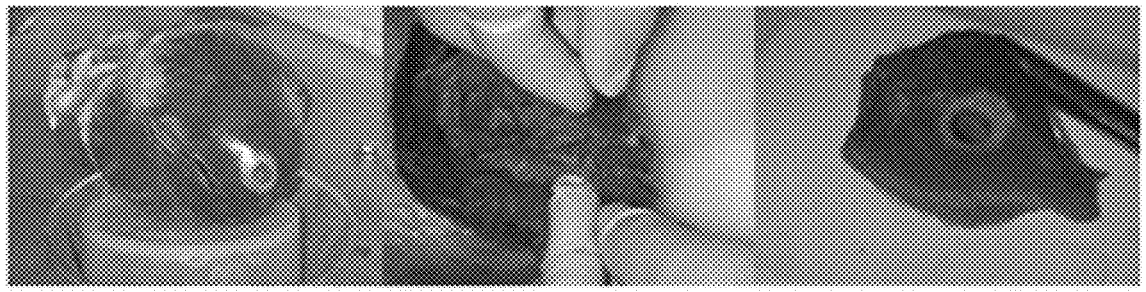

FIGS. 36 through 39 show the results of the method performed on the pig shown in FIGS. 28 through 34. FIG. 36 shows no leakage of blood through the sealing device about 1 hour after the procedure was completed. FIG. 37 shows an explanted heart and with the sealing device trimmed showing sufficient closure of the access channel. FIG. 38 shows the sealing device completely covering the access channel. FIG. 39 shows a controlled localized tissue treated with mechanical strengthening by energy application around the insertion site (the access channel).

Kits

According to some embodiments, one, some or all components of the system and device may be configured for single use or be disposable. In some embodiments, one, some or all components may be sterilized. According to some embodiments, a portion or combination of the single use items may be sold as kit.

In some embodiments, the kit may include a heart access device according to embodiments. The kit may include a sheath and at least one energy-transducing element. In further embodiments, the kit may further include an introducer. In some embodiments, the kit may include a sleeve. In some embodiments, the kit may include a sealing device. In some embodiments, the kit may include a sealing device introducer.

While various embodiments of the disclosure have been described, the description is intended to be exemplary rather than limiting and it will be apparent to those of ordinary skill in the art that many more embodiments and implementations are possible that are within the scope of the disclosure.

The invention claimed is:

1. A method for accessing a cardiac chamber or a vascular conduit of a heart for an interventional procedure, comprising:
   forming an access channel into a tissue of an apical area of the heart by inserting an instrument that includes at least one energy transducing element;
   advancing a sheath over the instrument within the access channel so that the at least one energy-transducing element of the instrument corresponds to a section of the sheath, the section being configured to contact and to transmit energy through the sheath to the tissue surrounding the sheath; and applying the energy from the instrument through the sheath to heat the tissue of the access channel surrounding the sheath so that the tissue of the access channel radially contracts around the sheath to mechanically enhance the access channel.

2. The method of claim 1, further comprising:
delivering a tissue-stabilizing composition prior to applying the energy,
wherein the energy is applied to the tissue-stabilizing composition.

3. The method of claim 1, wherein the energy includes microwave, ultrasound, RF, or heat energy.

4. The method of claim 1, wherein the energy includes ultrasound energy and the ultrasound energy heats the tissue surrounding the sheath.

5. The method of claim 1, wherein:
the sheath includes a section configured to transmit the energy delivered by the at least one energy-transducing element through the sheath to the surrounding tissue; and
the sheath is advanced so that the at least one energy-transducing element corresponds to the section of the sheath.

6. The method of claim 5, wherein the section contacts the at least one energy-transducing element when inserted.

7. The method of claim 1, further comprising:
inserting one or more instruments for the interventional procedure through the sheath provided in the mechanically enhanced access channel; and
removing a portion of the sheath so that a remaining portion of the sheath remains in the access channel after the access channel is sealed.

8. A method for accessing a cardiac chamber or a vascular conduit of a heart for an interventional procedure, comprising:
providing an access channel into a tissue of the apical area of the heart;
providing a heart access device within the access channel, the heart access device including at least one energy-transducing element being configured to deliver energy to tissue of the access channel surrounding the sheath;
applying the energy from the at least one energy-transducing element to heat the tissue of the access channel surrounding the heart access device so that the tissue of the access channel radially contracts around the heart access device to mechanically enhance the access channel;
inserting one or more instruments for the interventional procedure through the heart access device provided in the mechanically enhanced access channel; and
removing a portion of the heart access device so that a remaining portion of the heart access device remains in the access channel after the access channel is sealed.

9. The method of claim 8, further comprising:
delivering a tissue-stabilizing composition prior to applying the energy,
wherein the energy is applied to the tissue-stabilizing composition.

10. The method of claim 8, wherein the energy includes microwave, ultrasound, RF, or heat energy.

11. The method of claim 8, wherein the energy includes ultrasound energy and the ultrasound energy heats the tissue surrounding the sheath.

12. The method of claim 8, further comprising:
inserting a sealing device into the heart access device;
wherein the portion of the heart access device is removed after insertion of the sealing device.

13. The method of claim 8, wherein the heart access device includes a sheath and an introducer, the introducer including the energy-transducing element, the method further comprising:
forming an access channel into the tissue of an apical area of the heart by inserting the introducer that includes the energy-transducing element.

14. A method for accessing a cardiac chamber or a vascular conduit of a heart for an interventional procedure, comprising:
forming an access channel into a tissue of the chamber or the conduit by inserting an introducer that includes an energy-transducing element configured to deliver the energy;
advancing a sheath over the introducer so that the energy-transducing element of the introducer corresponds to a section of the sheath, the section being configured to contact and to transmit energy through the sheath to the tissue surrounding the sheath; and
applying the energy from the introducer through the sheath at the section to heat the tissue of the access channel surrounding the sheath so that the tissue of the access channel radially contracts around the sheath to mechanically enhance the access channel.

15. The method of claim 14, further comprising:
delivering a tissue-stabilizing composition prior to applying the energy,
wherein the energy is applied to the tissue-stabilizing composition.

16. The method of claim 14, wherein the access channel is in an apical area of the heart.

17. The method of claim 14, wherein:
the energy includes microwave, ultrasound, RF, or heat energy.

18. The method of claim 14, wherein the energy includes ultrasound energy and the ultrasound energy heats the tissue surrounding the sheath.

19. The method of claim 14, further comprising:
inserting one or more instruments for the interventional procedure through the sheath provided in the mechanically enhanced access channel; and
removing a portion of the sheath so that a remaining portion of the sheath remains in the access channel after the access channel is sealed.

* * * * *